US012558367B2

(12) United States Patent
Erickson et al.

(10) Patent No.: US 12,558,367 B2
(45) **Date of Patent: *Feb. 24, 2026**

(54) NICOTINAMIDE RIBOSIDE AND DERIVATIVES THEREOF IN INTRAVENOUS FORMULATIONS AND METHODS OF USE THEREOF

(71) Applicant: ChromaDex Inc., Los Angeles, CA (US)

(72) Inventors: Aron Erickson, Berthoud, CO (US); Philip Redpath, Firestone, CO (US); Yasmeen Maisha Nkrumah-Elie, Denver, CO (US); Andrew Earl Shao, Monrovia, MD (US)

(73) Assignee: ChromaDex Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/193,361

(22) Filed: Apr. 29, 2025

(65) Prior Publication Data

US 2025/0255896 A1 Aug. 14, 2025

Related U.S. Application Data

(63) Continuation of application No. 18/744,419, filed on Jun. 14, 2024.

(60) Provisional application No. 63/508,151, filed on Jun. 14, 2023.

(51) Int. Cl.
*A61K 31/706* (2006.01)
*A61K 9/00* (2006.01)
*A61K 31/7084* (2006.01)

(52) U.S. Cl.
CPC .......... *A61K 31/706* (2013.01); *A61K 9/0019* (2013.01); *A61K 31/7084* (2013.01)

(58) Field of Classification Search
None
See application file for complete search history.

(56) References Cited

U.S. PATENT DOCUMENTS

| | | | | |
|---|---|---|---|---|
| 8,106,184 | B2 | 1/2012 | Sauve et al. | |
| 9,408,834 | B2 | 8/2016 | Zemel et al. | |
| 9,861,651 | B2 | 1/2018 | Brown et al. | |
| 10,000,519 | B2 * | 6/2018 | Migaud | C07H 19/048 |
| 10,189,872 | B2 * | 1/2019 | Carlson | A61K 31/706 |
| 10,280,190 | B2 | 5/2019 | Dellinger et al. | |
| 10,316,054 | B2 | 6/2019 | Szczepankiewicz et al. | |
| 10,344,002 | B2 | 7/2019 | Zemel et al. | |
| 10,485,814 | B2 | 11/2019 | Szczepankiewicz et al. | |
| 10,668,096 | B2 | 6/2020 | Sauve et al. | |
| 11,071,718 | B2 | 7/2021 | Nandra et al. | |
| 11,260,069 | B2 | 3/2022 | Marcotulli et al. | |
| 11,414,407 | B2 | 8/2022 | Marcotulli et al. | |
| 2016/0272668 | A1 | 9/2016 | Dellinger et al. | |
| 2018/0147225 | A1 | 5/2018 | Brenner et al. | |
| 2019/0060336 | A1 | 2/2019 | Huizenga | |
| 2021/0000808 | A1 | 1/2021 | Gonzalez et al. | |
| 2022/0249535 | A1 | 8/2022 | Aronson et al. | |

FOREIGN PATENT DOCUMENTS

| | | | |
|---|---|---|---|
| WO | 2021202245 | A1 | 10/2021 |
| WO | 2022269064 | A1 | 12/2022 |
| WO | 2023064619 | A1 | 4/2023 |

OTHER PUBLICATIONS

Anselmo, Aaron C., and Samir Mitragotri. "An overview of clinical and commercial impact of drug delivery systems." Journal of Controlled Release 190 (2014): 15-28.*

Podyacheva, Ekaterina, et al. "Intravenous nicotinamide riboside administration has a cardioprotective effect in chronic doxorubicin-induced cardiomyopathy." International Journal of Molecular Sciences 23.21 (2022): 13096.*

Zapata-Pérez, Rubén, et al. "Reduced nicotinamide mononucleotide is a new and potent NAD+ precursor in mammalian cells and mice." The FASEB Journal 35.4 (2021): e21456.*

Adriouch, S., et al. "Extracellular NAD+: a danger signal hindering regulatory T cells." Microbes and infection 14.14 (2012): 1284-1292.

Adriouch, S., et al. "Rapid induction of naive T cell apoptosis by ecto-nicotinamide adenine dinucleotide: requirement for mono (ADP-ribosyl) transferase 2 and a downstream effector." The Journal of Immunology 167.1 (2001): 196-203.

Airhart, S. E., et al. "An open-label, non-randomized study of the pharmacokinetics of the nutritional supplement nicotinamide riboside (NR) and its effects on blood NAD+ levels in healthy volunteers." PloS one 12.12 (2017): e0186459, 17 pages.

Audrito, V., et al. "The extracellular NADome modulates immune responses." Frontiers in immunology 12 (2021): 704779, 13 pages.

Berven, H., et al. "NR-SAFE: a randomized, double-blind safety trial of high dose nicotinamide riboside in Parkinson's disease." Nature Communications 14.1 (2023): 7793, 13 pages.

Bieganowski, P., et al. "Discoveries of nicotinamide riboside as a nutrient and conserved NRK genes establish a Preiss-Handler independent route to NAD+ in fungi and humans." Cell 117.4 (2004): 495-502.

Bijă, A., et al. "Nicotinamide Riboside, a Promising Vitamin B3 Derivative for Healthy Aging and Longevity: Current Research and Perspectives." Molecules 28. 16 (2023): 6078.

Brakedal, B., et al. "The NADPARK study: A randomized phase I trial of nicotinamide riboside supplementation in Parkinson's disease." Cell metabolism 34.3 (2022): 396-407.

Cantó, C., et al. "The NAD+ precursor nicotinamide riboside enhances oxidative metabolism and protects against high-fat diet-induced obesity." Cell metabolism 15.6 (2012): 838-847.

(Continued)

*Primary Examiner* — Patrick T Lewis
(74) *Attorney, Agent, or Firm* — Amin Wasserman Gurnani LLP; George M. Carrera, Jr.; Jonathan J. Krit

(57) ABSTRACT

A stable intravenous (I.V.) composition includes nicotinamide riboside (NR) as described, or other nicotinyl riboside compounds which are NAD+ precursors, in said intravenous form. NR chloride may be provided in an intravenous (I.V.) formulation for administration to a human subject.

14 Claims, 11 Drawing Sheets

(56) References Cited

OTHER PUBLICATIONS

Conze, D., et al. "Safety and metabolism of long-term administration of Niagen (nicotinamide riboside chloride) in a randomized, double-blind, placebo-controlled clinical trial of healthy overweight adults." Scientific reports 9.1 (2019): 9772, 13 pages.
Damgaard, M. V., et al. "Intravenous nicotinamide riboside elevates mouse skeletal muscle NAD+ without impacting respiratory capacity or insulin sensitivity." IScience 25.2 (2022), 20 pages.
Elhassan, Y. S., et al. "Nicotinamide riboside augments the aged human skeletal muscle NAD+ metabolome and induces transcriptomic and anti-inflammatory signatures." Cell reports 28.7 (2019): 1717-1728.
Gasparrini, M., et al. "Enzymology of extracellular NAD metabolism." Cellular and Molecular Life Sciences 78.7 (2021): 3317-3331.
Grant, R., et al. "A pilot study investigating changes in the human plasma and urine NAD+ metabolome during a 6 hour intravenous infusion of NAD+." Frontiers in aging neuroscience 11 (2019): 257, 10 pages.
Heng, S. Y., et al. "Peripheral vein thrombophlebitis in the upper extremity: a systematic review of a frequent and important problem." The American journal of medicine 133.4 (2020): 473-484.
Kimura, S., et al. "Nicotinamide mononucleotide is safely metabolized and significantly reduces blood triglyceride levels in healthy individuals." Cureus 14.9 (2022), 11 pages.
Kropotov, A., et al. "Equilibrative nucleoside transporters mediate the import of nicotinamide riboside and nicotinic acid riboside into human cells." International Journal of Molecular Sciences 22.3 (2021): 1391, 13 pages.
Liu, Z-X, et al. "Extracellular nicotinamide adenine dinucleotide induces T cell apoptosis in vivo and in vitro." The Journal of Immunology 167.9 (2001): 4942-4947.
López-Otín, C., et al. "Hallmarks of aging: An expanding universe." Cell 186.2 (2023): 243-278.
Martens, C., et al. "Chronic nicotinamide riboside supplementation is well-tolerated and elevates NAD+ in healthy middle-aged and older adults." Nature communications 9.1 (2018): 1286, 11 pages.
McReynolds, M. R., et al. "Age-related NAD+ decline." Experimental gerontology 134 (2020): 110888, 19 pages.
Nadlinger, K., et al. "Influence of reduced nicotinamide adenine dinucleotide on the production of interleukin-6 by peripheral human blood leukocytes." Neuroimmunomodulation 9.4 (2002): 203-208.
Nikiforov, A., et al. "Pathways and subcellular compartmentation of NAD biosynthesis in human cells: from entry of extracellular precursors to mitochondrial NAD generation." Journal of Biological Chemistry 286.24 (2011): 21767-21778.
O'Hollaren, P. "Diphosphopyridine nucleotide in the prevention, diagnosis and treatment of drug addiction." West J Surg Obstet Gynecol (1961), 3 pages.
Ratajczak, J., et al. "NRK1 controls nicotinamide mononucleotide and nicotinamide riboside metabolism in mammalian cells." Nature communications 7.1 (2016): 13103, 12 pages.
Sauve, A. A., et al. "Triple-Isotope Tracing for Pathway Discernment of NMN-Induced NAD+ Biosynthesis in Whole Mice." International Journal of Molecular Sciences 24.13 (2023): 11114, 19 pages.
Tahir, N., et al. "Neutrophilia." (2021) Retrieved from the Internet on Sep. 3, 2024: URL: https://europepmc.org/article/nbk/nbk570571#free-full-text, 8 pages.
Trammell, S. AJ, et al. "Nicotinamide riboside is uniquely and orally bioavailable in mice and humans." Nature communications 7.1 (2016): 12948, 14 pages.
Wu, J., et al. "Boosting NAD+ blunts TLR4-induced type I IFN in control and systemic lupus erythematosus monocytes." The Journal of clinical investigation 132.5 (2022), 14 pages.
Third Party Submission Documents List under 37 CFR §1.290 for 19193361, Nov. 21, 2025, 38 pgs.

* cited by examiner

| Group | How did you feel during the IV – Frequency of side-effects | Did you feel any discomfort during the IV – frequency of side effects |
|---|---|---|
| NAD+ IV | 18 | 24 |
| NR IV | 12 | 10 |
| Saline | 5 | 2 |

FIG. 10

NICOTINAMIDE RIBOSIDE AND DERIVATIVES THEREOF IN INTRAVENOUS FORMULATIONS AND METHODS OF USE THEREOF

CROSS-REFERENCE TO RELATED APPLICATIONS

This application is a Continuation of U.S. application Ser. No. 18/744,419, filed on Jun. 14, 2024, which claims the benefit of U.S. Provisional Appl. 63/508,151, filed on Jun. 14, 2023, which are each hereby incorporated by reference herein in their entireties.

TECHNICAL FIELD

The present invention relates to a process for providing nicotinamide riboside (NR) or a salt or solvate thereof, in a stable form for intravenous administration, or other nicotinyl riboside compounds which are NAD+ precursors, in said intravenous form. NR chloride may be provided in an intravenous (I.V.) formulation for administration to a mammal, including a human subject.

BACKGROUND

Nicotinamide riboside (NR) is a valuable bioactive intermediate. This compound has been implicated in processing and metabolic pathways involving NAD+ (J. Preiss and P. Handler, *J. Biol. Chem.* (1958) 233:488-492). Nicotinic acid and nicotinamide, collectively niacins, are the vitamin forms of nicotinamide adenine dinucleotide (NAD+). Eukaryotes can synthesize NAD+de novo via the kynurenine pathway from tryptophan (Krehl, et al. *Science* (1945) 101:489-490; Schutz and Feigelson, *J. Biol. Chem.* (1972) 247:5327-5332) and niacin supplementation prevents the pellagra that can occur in populations with a tryptophan-poor diet. Thus, it is well-established that nicotinic acid is phosphoribosylated to nicotinic acid mononucleotide (NaMN), which is then adenylylated to form nicotinic acid adenine dinucleotide (NaAD), which in turn is amidated to form NAD+ (Preiss and Handler (1958) 233:488-492*; Ibid.,* 493-50).

Nicotinamide Adenine Dinucleotide ("$NAD^+$") is an enzyme co-factor that is essential for the function of several enzymes related to reduction-oxidation reactions and energy metabolism. (Katrina L. Bogan & Charles Brenner, *Nicotinic Acid, Nicotinamide, and Nicotinamide Riboside: A Molecular Evaluation of $NAD^+$ Precursor Vitamins in Human Nutritions,* 28 Annual Review of Nutrition 115 (2008)). $NAD^+$ functions as an electron carrier in cell metabolism of amino acids, fatty acids, and carbohydrates. (Bogan & Brenner 2008). $NAD^+$ serves as an activator and substrate for sirtuins, a family of protein deacetylases that have been implicated in metabolic function and extended lifespan in lower organisms. (Laurent Mouchiroud et al., *The $NAD^+$/Sirtuin Pathway Modulates Longevity through Activation of Mitochondrial UPR and FOXO Signaling,* 154 Cell 430 (2013)). The co-enzymatic activity of $NAD^+$, together with the tight regulation of its biosynthesis and bioavailability, makes it an important metabolic monitoring system that is clearly involved in the aging process.

Once converted intracellularly to $NAD(P)^+$, vitamin B3 is used as a co-substrate in two types of intracellular modifications, which control numerous essential signaling events (adenosine diphosphate ribosylation and deacetylation) and is a cofactor for over 400 reduction-oxidation enzymes, thus controlling metabolism. This is demonstrated by a range of metabolic endpoints including the deacetylation of key regulatory proteins, increased mitochondrial activity, and oxygen consumption. Critically, the NAD(P)(H)-cofactor family can promote mitochondrial dysfunction and cellular impairment if present in sub-optimal intracellular concentrations. Vitamin B3 deficiency yields to evidenced compromised cellular activity through $NAD^+$ depletion, and the beneficial effect of additional $NAD^+$ bioavailability through nicotinic acid ("NA"), nicotinamide ("Nam"), and nicotinamide riboside ("NR") supplementation is primarily observed in cells and tissues where metabolism and mitochondrial function had been compromised. Interestingly, supplementation with nicotinic acid ("NA") and nicotinamide ("Nam"), while critical in acute vitamin B3 deficiency, does not demonstrate the same physiological outcomes compared with that of nicotinamide riboside ("NR") supplementation, even though at the cellular level, all three metabolites are responsible for $NAD^+$ biosynthesis. This emphasizes the complexity of the pharmacokinetics and bio-distribution of B3-vitamin components.

The bulk of intracellular $NAD^+$ is believed to be regenerated via the effective salvage of nicotinamide ("Nam") while de novo $NAD^+$ is obtained from tryptophan. (Anthony Rongvaux ct al., *Reconstructing eukaryotic NAD metabolism,* 25 BioEssays 683 (2003)). Crucially, these salvage and de novo pathways apparently depend on the functional forms of vitamins B1, B2, and B6 to generate $NAD^+$ via a phosphoriboside pyrophosphate intermediate. Nicotinamide riboside ("NR") is the only form of vitamin B3 from which $NAD^+$ can be generated in a manner independent of vitamins B1, B2, and B6, and the salvage pathway using nicotinamide riboside ("NR") for the production of $NAD^+$ is expressed in most eukaryotes.

The main $NAD^+$ precursors that feed the salvage pathways are nicotinamide ("Nam") and nicotinamide riboside ("NR"). (Bogan & Brenner 2008). Studies have shown that nicotinamide riboside ("NR") is used in a conserved salvage pathway that leads to $NAD^+$ synthesis through the formation of nicotinamide mononucleotide ("NMN"). Upon entry into the cell, nicotinamide riboside ("NR") is phosphorylated by the NR kinases ("NRKs"), generating NMN, which is then converted to $NAD^+$ by nicotinamide mononucleotide adenylyltransferase ("NMNAT"). (Bogan & Brenner 2008). Because NMN is the only metabolite that can be converted to $NAD^+$ in mitochondria, nicotinamide ("Nam") and nicotinamide riboside ("NR") are the two candidate $NAD^+$ precursors that can replenish $NAD^+$ and thus improve mitochondrial fuel oxidation. A key difference is that nicotinamide riboside ("NR") has a direct two-step pathway to $NAD^+$ synthesis that bypasses the rate-limiting step of the salvage pathway, nicotinamide phosphoribosyltransferase ("NAMPT"). Nicotinamide ("Nam") requires NAMPT activity to produce $NAD^+$. This reinforces the fact that nicotinamide riboside ("NR") is a very effective $NAD^+$ precursor. Conversely, deficiency in dietary $NAD^+$ precursors and/or tryptophan causes pellagra, a disease characterized by dermatitis, diarrhea, and dementia. (Bogan & Brenner 2008). In summary, $NAD^+$ is required for normal mitochondrial function, and because mitochondria are the powerhouses of the cell, $NAD^+$ is required for energy production within cells. $NAD^+$ was initially characterized as a co-enzyme for oxidoreductases. Though conversions between $NAD^+$, NADH, NADP and NADPH would not be accompanied by a loss of total co-enzyme, it was discovered that $NAD^+$ is also turned over in cells for unknown purposes (Maayan, Nature (1964) 204:1169-1170). Sirtuin enzymes such as Sir2 of *S. cerevisiae* and its homologs deacetylate lysine residues with consumption of an equivalent of $NAD^+$ and this activity is required for Sir2 function as a transcriptional silencer (Imai, et al., *Cold Spring Harb. Symp. Quant. Biol.* (2000) 65:297-302). $NAD^+$-dependent deacetylation reactions are required not only for alterations in gene expression but also for repression of ribosomal DNA recombination and extension of lifespan in response to calorie restriction (Lin, et al., *Science* (2000) 289:2126-2128; Lin, et al., *Nature* (2002) 418:344-348). $NAD^+$ is consumed by Sir2 to produce a mixture of 2'- and 3' O-acetylated ADP-ribose plus nicotinamide and the deacetylated polypeptide (Sauve, et al., *Biochemistry* (2001) 40:15456-15463). Additional enzymes, including poly(ADPribose) polymerases and cADPribose synthases are also $NAD^+$-dependent and produce nicotinamide and ADPribosyl products (Ziegler, *Eur. J. Biochem.* (2000) 267:1550-1564; Burkle, Bioessays (2001) 23:795-806).

The non-coenzymatic properties of $NAD^+$ has renewed interest in $NAD^+$ biosynthesis. FIG. 1 describes how NAR, NR and other metabolic intermediates are transformed to $NAD^+$. In short, the biosynthetic pathway for NAR proceeds directly to NaMN, then NaAD, and ultimately to form $NAD^+$.

Certain medications produce specific sensations of pain associated with their intravenous (I.V.) administration. This includes potassium, which when administered I.V. can cause a burning or painful sensation (Heng S Y, Yap R T, Tie J, McGrouther D A (April 2020). "Peripheral Vein Thrombophlebitis in the Upper Extremity: A Systematic Review of a Frequent and Important Problem". *The American Journal of Medicine.* 133 (4): 473-484). The incidence of side effects specific to a medication can be affected by the type of access (peripheral vs. central), the rate of administration, or the quantity of drug administered. When medications are administered too rapidly through an I.V. line, a set of vague symptoms such as redness or rash, fever, and others may occur; this is termed an "infusion reaction" and is often prevented by decreasing the rate of administration of the medication.

If NR, or its derivatives, salts, or prodrugs thereof, as described herein, could be developed in a stable intravenous (I.V.) formulation, or alternatively, a reconstitutable formulation for use in intravenous administration, e.g., in order to enhance NAD+ levels in cells, and administrable with a minimum of painful or uncomfortable side-effects or symptoms, this would represent a useful contribution to the art.

SUMMARY

A composition comprises NR, or a salt or solvate thereof, in a stable aqueous-based intravenous (I.V.) formulation. In an embodiment, the I.V. formulation contains a stable crystalline powder form of NR which may be reconstituted in an aqueous-based formulation for IV administration.

In one embodiment, the composition comprises NR, or a salt or solvate thereof, in a stable, solid reconstitutable form for use in an aqueous-based intravenous (I.V.) formulation.

In yet another embodiment, a method is described for making a composition comprising an aqueous intravenous (I.V.) formulation containing a compound selected from nicotinamide riboside, a salt thereof, or a solvate thereof, or derivatives thereof (including reduced, 1-4-dihydropyridine forms) comprising the steps of: (a) providing nicotinamide riboside (NR), a salt thereof, or a solvate thereof, in a crystalline or amorphous form; (b) adding water or an aqueous-based liquid to dissolve the NR, a salt thereof, or a solvate thereof. Optionally, a solid or liquid inert carrier may be employed such as a stabilizer and/or buffer.

In one embodiment, NR is produced by a sterilization process. The NR structure and stability survives the sterilization process. The sterilization process is carried out on the dried NR-Cl powder using e-beam or gamma irradiation. The sterile water added and mixed within the vial is produced any number of ways including distillation and/or chemical treatment. In one embodiment, the sterilization includes, but is not limited to, lyophilization, gamma irradiation, e-beam irradiation, heat sterilization. In one embodiment, a sterile filtration of premixed water and NR is produced.

In a further embodiment, a method for I.V. administration of NR, a salt thereof, or a solvate thereof to a human subject, comprising: (a) providing an aqueous-based I.V. formulation containing NR, a salt thereof, or a solvate thereof; (b) intravenously administering an effective amount of the I.V. formulation to the human subject in such a manner that the pain response or generalized discomfort (or other side effects causing discomfort) are minimized and/or comfort level maintained in the human subject; and (c) continuously measuring and monitoring the pain response and/or comfort level of the human subject during the I.V. administration of the I.V. formulation to ensure that the pain response is minimized. Pain response measurements may include a numerical variable analog scale (VAS) pain scale level.

In other embodiments, derivatives of NR may be used in a stable aqueous-based I.V. formulation, such as, but not limited to, 1-(2',3',5'-triacetyl-beta-D-ribofuranosyl)-nicotinamide ("NR triacetate" or "NRTA"), Nicotinic acid riboside (NAR), 1,4-dihydropyridyl reduced nicotinamide riboside ("NRH"), or 1,4-dihydropyridyl reduced nicotinic acid riboside ("NARH").

BRIEF DESCRIPTION OF THE FIGURES

FIG. 10 depicts the frequency of side effects reported for the $NAD^+$ IV, NR IV and saline test groups during administration. Side effects include chest tightness, nausea, digestive discomfort, tingling, muscle soreness, cold arm, burning/cool sensation, head pressure, burning tongue/jaw, headache, hot flashes, fatigue, chills, nasal congestion and dizziness.

DETAILED DESCRIPTION

Figure 1:
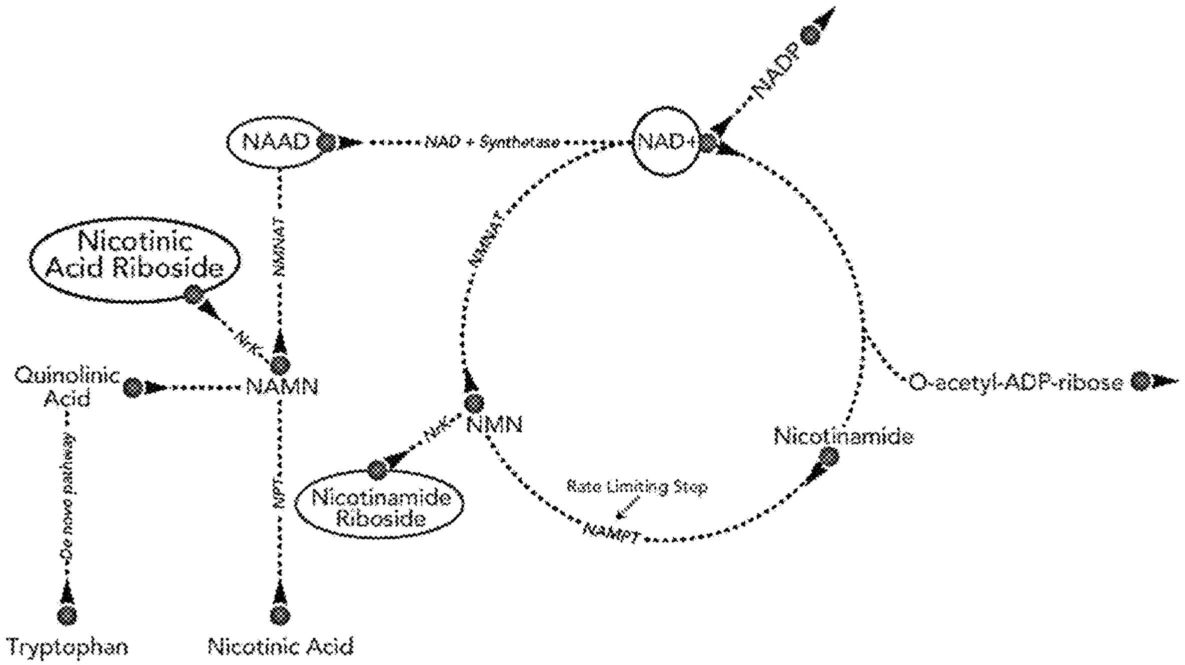
FIG. 1 depicts the $NAD^+$ biosynthetic pathway. Nicotinic acid riboside (NAR) and nicotinamide riboside (NR) are shown.

Nicotinamide riboside ("NR") is a pyridinium compound having the formula (I):

(I)

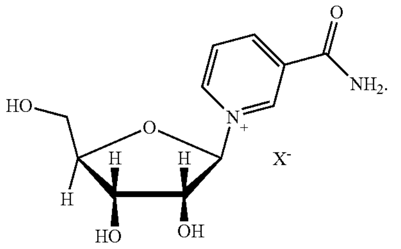

NR of formula (I) can include salts or solvates. Salts may include counterions (defined as "X—") selected from chloride, bromide, iodide, and the like. For example, one useful salt is the chloride salt of NR ("NR-Cl"). Further salts may include, but are not limited to, fluoride, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfate, tartrate, hydrogen tartrate, malate, hydrogen malate, maleate, fumarate, citrate, stearate, palmitate, myristate, laurate, caprate, caprylate, caproate, oleate, linoleate, sulfonate, trifluoromethanesulfonate, trichloromethanesulfonate, tribromomethanesulfonate, trichloroacetate, tribromoacetate, and trifluoroacetate. For NAR, NAMN and NMN, and the like, optionally wherein when X— is absent, optionally the counterion is an internal salt, and/or zwitterion.

NR requires a pharmaceutically acceptable and stable formulation for human use. For example, a stable, aqueous-based formulation is provided herein, comprising NR, a salt thereof, or a solvate thereof, suitable for human use in an I.V. formulation.

In one embodiment, NR is available in an I.V. formulation as Niagen®+IV (a.k.a. "NR IV"). Furthermore, Niagen® which is nicotinamide riboside chloride is the sole active ingredient in the consumer product Tru Niagen®, available from ChromaDex, Inc. (Los Angeles, California).

In a further aspect, derivatives of NR are contemplated having the formula (Ia) or a salt, solvate, or prodrug thereof:

(Ia)

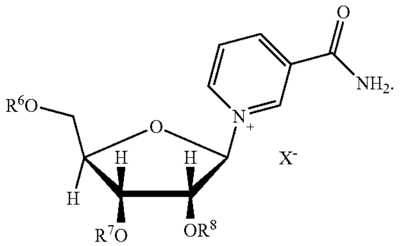

wherein $R^6$ is selected from the group consisting of hydrogen, C(O)R', C(O)OR', —C(O)NHR', substituted or unsubstituted ($C_1$-$C_8$)alkyl, substituted or unsubstituted ($C_1$-$C_5$) cycloalkyl, substituted or unsubstituted aryl, substituted or unsubstituted heteroaryl, and substituted or unsubstituted heterocycle, suitable substituents include, but are not limited to, alkyl, alkylaryl, aryl, heteroaryl, halide, hydroxyl, carboxylate, carbonyl (including alkylcarbonyl and arylcarbonyl), phosphate, amino (including alkylamino, dialkylamino, hydroxylamino, dihydroxylamino, alkyl hydroxylamino, arylamino, diarylamino and alkylarylamino), thiol (including alkylthiol, arylthiol and thiocarboxylate), sulfate, nitro, cyano and azido;

R' is selected from the group consisting of hydrogen, —($C_1$-$C_{24}$)alkyl, —($C_1$-$C_5$) cycloalkyl, aryl, heteroaryl, heterocycle, aryl($C_1$-$C_4$)alkyl, and heterocycle ($C_1$-$C_4$)alkyl; and $R_7$ and $R_5$ are independently selected from the group consisting of hydrogen, —C(O)R', —C(O)OR', —C(O)NHR', substituted or unsubstituted ($C_1$-$C_{24}$)alkyl, substituted or unsubstituted ($C_1$-$C_5$) cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle ($C_1$-$C_4$)alkyl. Salts may include counterions (defined as "X—") selected from chloride, bromide, iodide, and the like, as discussed above.

This disclosure also includes other NAD+ precursors, such as, but not limited to, one or more nicotinyl riboside compounds selected from nicotinic acid riboside (NAR, II), nicotinamide mononucleotide (NMN, III), Reduced nicotinamide mononucleotide (NMNH), nicotinic acid mononucleotide (NaMN, IV), Reduced nicotinic acid mononucleotide (NaMNH), reduced nicotinamide riboside (NRH, V), reduced nicotinic acid riboside (NARH, VI), NR triacetate (NRTA, VII which is a species of Ia), NAR triacetate (NARTA, VIII), NRH triacetate (NRH-TA, IX), or NARH triacetate (NARH-TA, X), and salts, solvates, or mixtures thereof, or derivatives thereof. The salt for NMNH and NAMNH includes, but is not limited to, one or more of sodium, potassium, lithium, magnesium, calcium, strontium, barium or a nitrogen containing cation. In one embodiment, nitrogen containing cation can include substituted or unsubstituted ammonium, a substituted or unsubstituted pyridinium, a substituted or unsubstituted pyrollidinium, a substituted or unsubstituted imidazolium or the like.

Nicotinic acid riboside (NAR) is a pyridinium nicotinyl compound having the formula (II):

(II)

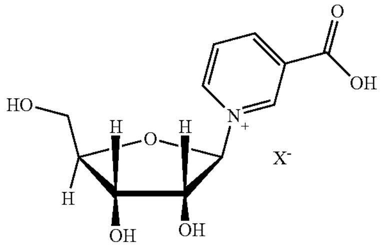

Further, where $X^-$ is absent, NAR is an inner salt (zwitterion). Further addition salts may include, but are not limited to sodium, potassium, lithium, magnesium, calcium, strontium, barium or a nitrogen containing cation.

Nicotinamide mononucleotide (NMN) is a pyridinium nicotinyl compound having the formula (III):

(III)

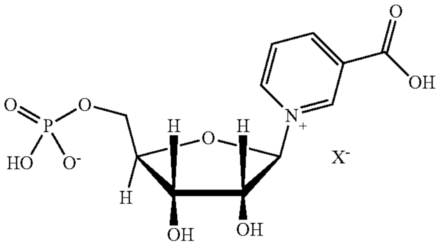

Further, where $X^-$ is absent, NMN is an inner salt (zwitterion). Further phosphate addition salts may include, but are not limited to one or more of sodium, potassium, lithium, magnesium, calcium, strontium, barium or a nitrogen containing cation.

Nicotinic acid mononucleotide (NaMN) is a pyridinium nicotinyl compound having the formula (IV):

(IV)

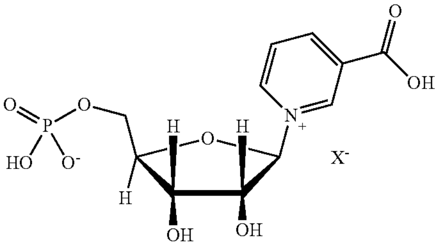

Further, where $X^-$ is absent, NAMN is an inner salt (zwitterion). Further phosphate addition salts may include, but are not limited to one or more of sodium, potassium, lithium, magnesium, calcium, strontium, barium or a nitrogen containing cation.

Reduced nicotinamide riboside ("NRH") is a 1,4-dihydropyridyl reduced nicotinyl compound having the formula (V):

(V)

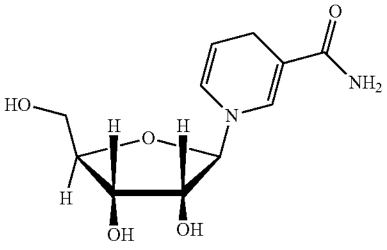

Reduced nicotinic acid riboside ("NARH") is a 1,4-dihydropyridyl reduced nicotinyl compound having the formula (VI):

(VI)

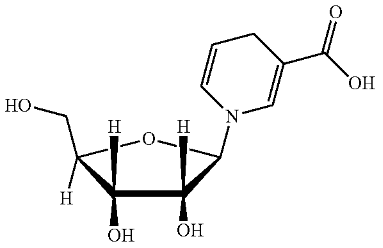

Further addition salts may include, but are not limited to sodium, potassium, lithium, magnesium, calcium, strontium, barium or a nitrogen containing cation.

In a species of compound (Ia), the free hydrogens of hydroxyl groups on the ribose moiety of nicotinamide riboside (NR, I) can be substituted with acetyl groups ($CH_3—C(=O)—$) to form 1-(2',3',5'-triacetyl-beta-D-ribofuranosyl)-nicotinamide ("NR triacetate" or "NRTA") having the formula (VII):

(VII)

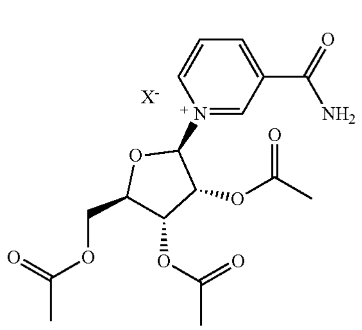

The free hydrogens of hydroxyl groups on the ribose moiety of nicotinic acid riboside (NAR, II) can be substituted with acetyl groups ($CH_3—C(=O)—$) to form 1-(2',3',5'-triacetyl-beta-D-ribofuranosyl)-nicotinic acid ("NAR triacetate" or "NARTA") having the formula (VIII):

(VIII)

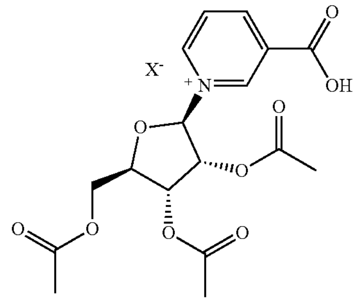

Further, where $X^-$ is absent, NARTA is an inner salt (zwitterion). Further addition salts may include, but are not limited to sodium, potassium, lithium, magnesium, calcium, strontium, barium or a nitrogen containing cation.

The free hydrogens of hydroxyl groups on the ribose moiety of reduced nicotinamide riboside (NRH, V) can be substituted with acetyl groups ($CH_3—C(=O)—$) to form 1-(2',3',5'-triacetyl-beta-D-ribofuranosyl)-1,4-dihydronicotinamide ("NRH triacetate" or "NRH-TA") having the formula (IX):

(IX)

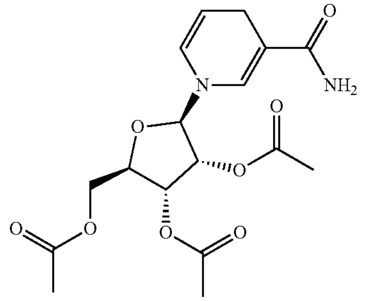

The free hydrogens of hydroxyl groups on the ribose moiety of reduced nicotinic acid riboside (NARH, VI) can be substituted with acetyl groups ($CH_3—C(=O)—$) to form 1-(2',3',5'-triacetyl-beta-D-ribofuranosyl)-1,4-dihydronicotinic acid ("NARH triacetate" or "NARH-TA") having the formula (X):

(X)

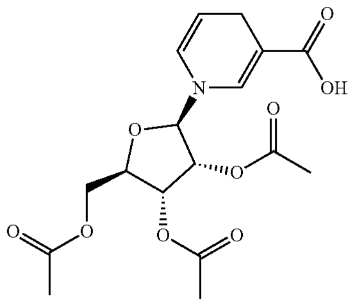

Further addition salts may include, but are not limited to sodium, potassium, lithium, magnesium, calcium, strontium, barium or a nitrogen containing cation.

For each of nicotinamide riboside (NR, I), nicotinic acid riboside (NAR, II), nicotinamide mononucleotide (NMN, III), nicotinic acid mononucleotide (NaMN, IV), reduced nicotinamide riboside (NRH, V), reduced nicotinic acid riboside (NARH, VI), nicotinamide riboside triacetate (NRTA, VII), nicotinic acid riboside triacetate (NARTA, VIII), reduced nicotinamide riboside triacetate (NRH-TA, IX), and reduced nicotinic acid riboside triacetate (NARH-TA, X), optionally X— as counterion is absent, or when X— is present, X— is selected from the group consisting of bromide, iodide, fluoride, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfate, tartrate, hydrogen tartrate, malate, hydrogen malate, maleate, fumarate, citrate, stearate, palmitate, myristate, laurate, caprate, caprylate, caproate, oleate, linoleate, sulfonate, trifluoromethanesulfonate, trichloromethanesulfonate, tribromomethanesulfonate, trichloroacetate, tribromoacetate, and trifluoroacetate; and, optionally wherein when X− is absent, optionally the counterion is an internal salt or zwitterion;

optionally $X^-$ is an anion of a substituted or unsubstituted carboxylic acid selected from monocarboxylic acid, a dicarboxylic acid, or a polycarboxylic acid;

optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, or trifluoroacetate; and, optionally $X^-$ is an anion of an unsubstituted monocarboxylic acid selected from formic acid, acetic acid, propionic acid, or butyric acid, the anions being formate, acetate, propionate, butyrate, and stearate, and the like, respectively; or an anion of a long chain fatty acid including saturated, unsaturated and polyunsaturated fatty acids with carbon chain lengths of $C_6$-$C_{24}$ (such as, for example, stearic acid, palmitic acid, myristic acid, lauric acid, capric acid, caprylic acid, caproic acid, oleic acid, linoleic acid, omega-6 fatty acid, omega-3 fatty acid; the anions being stearate, palmitate, myristate, laurate, caprate, caprylate, caproate, oleate, linoleate, etc.); and, optionally X− is an anion of a substituted or unsubstituted amino acid, i.e., amino-monocarboxylic acid or an amino-dicarboxylic acid, optionally selected from glutamic acid and aspartic acid, the anions being glutamate and aspartate, respectively; or, alternatively, selected from alanine, beta-alanine, arginine, asparagine, cysteine, glutamine, glycine, histidine, isoleucine, leucine, lysine, methionine, phenylalanine, proline, serine, threonine, tryptophan, or tyrosine, and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate.

optionally $X^-$ is an anion of a substituted or unsubstituted sulfate, further optionally hydrogen sulfate.

optionally $X^-$ is an anion of a substituted or unsubstituted phosphate, further optionally dihydrogen phosphate or monohydrogen phosphate.

For each of the forgoing structures (II), (III), (IV), (V), (VI), (VII), (VIII), (IX), and (X), substituted derivatives and/or analogues thereof, respectively, are contemplated as useful for I.V. compositions, as described herein, or useful for methods of I.V. compositions or formulations comprising one or more of said compounds, as described herein.

It has been reported (anecdotally) that the direct I.V. administration of NAD+ to human subjects, over about 4 hours, using standard I.V. infusion techniques, causes significant pain and/or inflammation in the subject. Inflammation markers that are believed to be affected include, but are not limited to: IL-1 Beta, IL-2, IL-4, IL-6, IL-8, IL-10, IL-12, IL-13, TNF-alpha, TNF-beta, IFN-alpha, IFN-gamma, IFN-gamma, VEGF, PDGF, GSCF, FGF2, CSF, MCP-1, chemokines (including subfamilies CXCL, CCL), C-reactive protein (CRP), serum amyloid A, erythrocyte sedimentation rate (ESR) and the like. Nevertheless, in an effort to mitigate or lessen pain, or moreover to solve that problem of producing pain, combinations of NR (I), or compounds/formulas (II-X), NMNH and NAMNH, or salts or solvates thereof, with or without NAD+ are also contemplated for I.V. administration in accordance with the methods described herein.

Other suitable delivery systems are contemplated. For example, liposomes in the form of liposomal encapsulation may be employed. In an embodiment, dispersible lipid nanoparticles are used.

Notably, I.V. formulations without NAD+ present are preferred. Compounds NR (I), or compounds/formulas (II-X), NMNH and NAMNH, or salts or solvates thereof, can be administered as alternatives to NAD+ to alleviate the known (or anecdotal) negative issues involved with NAD+ I.V. administration (e.g., pain, inflammation, prolonged time of administration, etc.). For example, certain negative effects of extracellular NAD+ may include producing an inflammatory response. It is expected that these negative responses including pain and inflammation will be mitigated by NR-containing formulations. See, Nadlinger, et al., "Influence of reduced nicotinamide adenine dinucleotide on the production of interleukin-6 by peripheral human blood leukocytes," *Neuroimmunomodulation* (2001) 9 (4): 203-208; Adriouch, et al., "Extracellular NAD (+): a danger signal hindering regulatory T cells," *Microbes Infect*. (2012 November) 14 (14): 1284-1292.

In other embodiments, the preferred I.V. formulations described herein may be used to improve recovery time from exercise, promote enhanced performance, improve levels of fatigue/exhaustion, enhance mental abilities, improve cognitive skills such as memory, reduce stress, or improve sleep or sleep patterns. It is expected that any or all of these conditions would be improved using the preferred I.V. formulations without NAD+ and in comparison to NAD+ I.V. administration alone.

In this context, inflammation, both specific (e.g., phlebitis on injection) or generalized in situ, can be problematic when injecting NAD+ into a human subject. Therefore, in the I.V. formulations containing combinations of NR (I), or compounds/formulas (II-X), NMNH and NAMNH, or salts or solvates thereof, with NAD+, it is anticipated that inflammation, both general and specific, and other inflammatory response or processes, will be reduced in the human subject, compared to I.V. administration of NAD+ alone.

In order to further modulate or prevent the inflammatory response, the I.V. formulations provided herein, which may include NR (I) and salts or solvates thereof, or combinations of NR (I) and at least one nicotinyl compound/formula (II-X), NMNH and NAMNH, or salts or solvates thereof, and/or combinations of the aforementioned with NAD+, may be further combined, co-administered, or sequentially administered with an anti-inflammatory agent. Useful anti-inflammatory agents may include, but are not limited to, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, α-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, carprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocortolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydrocortamate, hydrocortisone, hydrocortisone acetate, hydrocortisone succinate, hydrocortisone hemi succinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacyl-morphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicyl sulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In order to further modulate or prevent a proliferative response, the I.V. formulations provided herein, which may include NR (I) and salts or solvates thereof, or combinations of NR (I) and at least one nicotinyl compound/formula (II-X), or salts or solvates thereof, and/or combinations of the aforementioned with NAD+, may be further combined with an anti-cancer or chemotherapeutic agent. Chemotherapeutic agents that may be coadministered or sequentially administered with NR (I) and salts or solvates thereof, described herein as having anti-cancer activity (e.g., compounds that induce apoptosis, compounds that reduce lifespan or compounds that render cells sensitive to stress) include: aminoglutethimide, amsacrine, anastrozole, asparaginase, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine. These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disrupters such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In addition, the I.V. formulations may include longevity agents, anti-aging agents, and cell senescence modulating agents. Other therapeutic agents may be included such urolithin A, urolithin B, quercetin, metformin, and the like.

It has been reported (anecdotally) that the direct I.V. administration of NAD+ to human subjects, over about 4 hours, using standard I.V. infusion techniques, produces a feeling of euphoria or general well-being in the subject. It is believed that the I.V. formulations of the present disclosure containing combinations of NR (I), or compounds/formulas (II-X), or salts or solvates thereof, administered intravenously with or without NAD+ in accordance with the methods described herein, may also produce a feeling of euphoria or general well-being in the subject, but without the unintended negative side effects discussed above, such as pain responses, or inflammatory responses.

Notably, I.V. formulations without NAD+ present are preferred. Compounds NR (I), or compounds/formulas (II-X), or salts or solvates thereof, can be administered as alternatives to NAD+ to alleviate the known (anecdotal) issues involved with NAD+ I.V. administration (e.g., pain, inflammation, prolonged time of administration, etc.).

I.V. formulations of the present disclosure containing combinations of NR (I), or compounds/formulas (II-X), or salts or solvates thereof, with or without NAD+ in accordance with the methods described herein, may be combined with electrolytes, vitamins (such as B12 and others discussed below), antioxidants, and the like.

Formulations may be prepared as any product form suitable for use in human individuals, including reconstitutable powders, ready-to-drink liquids, parenteral (intravenous) formulations, and dilutable liquid concentrates, product forms which are all well known in the nutritional formula art. As used in the present application, the amounts of components present in formulations or compositions refer to the amounts when the formulation or composition is ready for consumption by the human individual.

Intravenous Embodiments

Large-volume injections intended to be administered by intravenous infusion commonly are called "I.V. fluids" and are included in the group of sterile and/or bacteriostatic products referred to as large-volume parenterals. These generally consist of single-dose injections having a volume of 100 mL or more and containing no added substances, intending to serve as a liquid carrier or inert pharmaceutical or nutritional vehicle. Intravenous fluids are generally packaged in containers having a capacity of about 100 to 1000 mL.

In its principal embodiment, NR may be provided dissolved in an I.V. fluid in an intravenous (I.V.) formulation for administration to a human subject. A composition comprises NR, or a salt or solvate thereof, in a stable aqueous-based intravenous (I.V.) formulation. The composition may include water or a water-based carrier, such as a pharmaceutically acceptable I.V. fluid or buffer solution. Water used for packaging is typically Water for Injection ("WFI"). Exemplary I.V. fluids or carriers may include, but are not limited to, water (e.g., USP grade, sterile, pyrogen-free), normal Saline, half normal Saline, Dextrose (e.g., 5% Dextrose or glucose, a.k.a. D5W or D5/W), Mannitol, Ringer's, Lactated Ringer's solution (a.k.a. Ringer's lactate), Ringer's acetate, Sodium lactate, Sodium bicarbonate, sterile and/or bacteriostatic water, and the like.

Useful vitamins may include Vitamin B3, which is also known as "nicotinic acid," or "niacin," and is a pyridine compound. It will be apparent to those skilled in the art that vitamin B3 is functionally and chemically inequivalent to, and not interchangeable with, nicotinamide riboside (NR, I), NR-X salts, or derivatives thereof. Other useful vitamins include Vitamins B1, B2, B5, B6, B7, B9, B12, $A_1$, C, $D_3$, $D_2$, E, and $K_1$.

Without being bound by theory, vitamins B1, B2, B3, and B6 are believed to be closely intertwined in their biosynthetic pathways, with the maintenance and regeneration of the NAD(P)(H) intracellular pool depending on the availability of ThDP (B1), FAD (B2), and PLP (B6). Thiamine (vitamin B1), riboflavin (vitamin B2), and pyridoxine (vitamin B6) are salvaged from food and converted back intracellularly to their respective, bioactive forms: Thiamine (ThDP); Flavin Adenine Dinucleotide (FAD); Nicotinamide Adenine Dinucleotide ($NAD^+$); and PyridoxaL Phosphate (PLP). The conversion of vitamins B1, B2, and B6 to ThDP, FAD, and PLP, respectively, is ATP-dependent. Two of the three salvage pathways that convert vitamin B3 to $NAD^+$ are dependent on ThDP (B1), with the de novo production of $NAD^+$ from tryptophan depending on the bioactive forms of vitamins B1, B2, and B6. The vitamin B1 dependency comes from the fact that ThDP (B1) is cofactor for the transketolases involved in the biosynthesis of phosphoriboside pyrophosphate, an essential substrate in these aforementioned $NAD^+$ salvage and de novo pathways.

Formulations or compositions can optionally be sterilized and subsequently used on a ready-to-feed basis, or can be stored as concentrates or powders. Concentrates can be prepared by spray drying a liquid formulation prepared as described herein, and a formulation can be reconstituted by rehydrating the concentrate. The formulation concentrate is a stable liquid and has a suitable shelf life. Reconstitutable powders may be prepared by lyophilization or freeze-drying. The formulation reconstitutable powder is a stable solid powder and has a suitable shelf life. Reconstitutable powders (apart from any fillers or stablilizers) can be prepared in unit dosages of 25 mg, 50 mg, 75 mg, 100 mg, 150 mg, 200 mg, 250 mg, 300 mg, 400 mg, 500 mg, 600 mg, 700 mg, 750 mg, 800 mg, 1000 mg, 1500 mg, 2000 mg, 2500 mg, up to 3000 mg. The reconstitutable powder may be reconstituted in a small volume of water, ethyl alcohol, DMSO, or an aqueous buffer suitable for dilution into an aqueous I.V. formulation.

Powders or lyophilized preparations made in accordance with this disclosure may be stored at room temperature (25° C.), refrigerated, or frozen for later use (e.g., −15° C., or −30° C.).

In the I.V. formulations of this disclosure, NR chloride may be crystalline, that is, the final product may be derived from a crystalline NR component.

Dosages of NR chloride as crystalline Form I and/or Form II in an I.V. formulation may range from about 25 mg to about 3 g per infusion over about 1-2 hours. In preferred embodiments, the dosage for infusion can be 25 mg, 50 mg, 75 mg, 100 mg, 150 mg, 200 mg, 250 mg, 300 mg, 400 mg, 500 mg, 600 mg, 700 mg, 750 mg, 800 mg, 1000 mg, 1500 mg, 2000 mg, 2500 mg, up to 3000 mg.

Apart from I.V. formulations, compositions for oral formulations useful for delivering an NR-containing composition can be orally administered, for example, with an inert diluent or with an assimilable edible carrier, or it can be enclosed in hard or soft shell gelatin or hydroxypropyl methylcellose (i.e., hypromellose) capsules, or it can be compressed into tablets, or it can be incorporated directly with the food of the diet. For oral administration, an NR-containing composition may be incorporated with an excipient and used in the form of ingestible tablets, buccal tablets, troches, capsules, elixirs, suspensions, syrups, wafers, and the like. The tablets, troches, pills, capsules, and the like can also contain the following: a binder such as gum tragacanth, acacia, corn starch, or gelatin; excipients such as dicalcium phosphate, microcrystalline cellulose, and the like; a disintegrating agent such as potato starch, alginic acid, and the like; a lubricant such as magnesium stearate; and a sweetening agent such as sucrose, lactose, or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the active compound, sucrose as a sweetening agent, methyl and propylparabens as preservatives, a dye, and flavoring such as cherry or orange flavor. Oil-in-water emulsions may be better for oral use in infants because these are water-miscible, and thus their oiliness is masked. Such emulsions are well known in the pharmaceutical sciences.

One goal of the present I.V. formulations is to treat a condition or disease in an animal, such as a mammal. Animal subjects include large domestic or agricultural mammals, for example, cows or cattle (or other bovine species), horses, pigs, sheep, goats, other livestock, and the like. Thus, animal subjects may include companion animals and animals used for sport (e.g., horses or dogs). Animal subjects may also include smaller domestic mammals, such as, but not limited to, dogs, cats, rabbits, and rodents including rats, mice, hamsters, gerbils, guinea pigs, and the like. The mammal may be a human subject. Exemplary conditions or diseases in need of I.V. treatment may include, but are not limited to, treatment for addictions such as drugs and/or alcohol. Thus, I.V formulations providing NR and/or a nicotinyl compound (I-X) or a derivative, prodrug or salt thereof may be used to treat addiction or withdrawal from addiction, or to treat addiction withdrawal symptoms, or treatment of alcoholic withdrawal or hangovers.

Other routes of parenteral administration for providing nutrition are contemplated. The compounds may be administered by any parenteral route by injection or infusion, including but not limited to intravenous, intramuscular, intraparenchymal, intraarterial, intraperitoneal, intranasal, intravaginal, intravesical (e.g., to the bladder), intradermal, transdermal, topical, or subcutaneous administration.

Further embodiments contemplate a kit for I.V. infusion or injection and/or subcutaneous or intramuscular or intradermal injections. In an embodiment, a kit is designed for I.V. infusion administration to a human subject of a therapeutically effective amount of nicotinamide riboside chloride salt (or other salts, or derivatives thereof, including reduced analogues), said kit comprising nicotinamide riboside chloride salt (NR-Cl), an injectable aqueous intravenous fluid contained in an I.V. bag; and a venous needle suitably connected to the I.V. bag for installation in a vein of the human subject for administration by I.V. infusion to the human subject. The nicotinamide riboside chloride salt may be crystalline Form I. In a preferred embodiment, the crystalline Form I nicotinamide riboside chloride salt is contained in the aqueous intravenous fluid in the I.V. bag for administration to the human subject.

In other embodiments, a kit is designed for subcutaneous injection administration to a human subject of a therapeutically effective amount of nicotinamide riboside chloride salt (or other salts, or derivatives thereof, including reduced analogues), said kit comprising nicotinamide riboside chloride salt (NR-Cl), an injectable aqueous intravenous fluid or aqueous parenteral fluid; and a hypodermic syringe having a needle for subcutaneous injection in the human subject. The nicotinamide riboside chloride salt may be crystalline Form I. In a preferred embodiment, the crystalline Form I nicotinamide riboside chloride salt is contained in the aqueous intravenous fluid or aqueous parenteral fluid which is contained in the hypodermic syringe for administration by subcutaneous injection to the human subject.

The embodiments of the present methods for treating and/or preventing symptoms, diseases, disorders, or conditions associated with, or having etiologies involving, vitamin B3 deficiency and/or that would benefit from increased mitochondrial activity in a mammalian subject, e.g. human, comprising administering or providing NR and/or a nicotinyl compound (I-X) or a derivative, prodrug or salt thereof alone or in combination with a vitamin described herein have not been demonstrated before.

Additionally, the embodiments of the present methods for treating and/or preventing symptoms, diseases, disorders, or conditions associated with, or having etiologies involving, vitamin B3 deficiency and/or that would benefit from increased mitochondrial activity in a mammalian subject address limitations of existing technologies to treat or prevent symptoms, diseases, disorders, or conditions associated with, or having etiologies involving, vitamin B3 deficiency and/or that would benefit from increased mitochondrial activity.

In certain embodiments, the present invention provides methods for treating and/or preventing symptoms, diseases, disorders, or conditions associated with, or having etiologies involving, vitamin B3 deficiency. Exemplary symptoms, diseases, disorders, or conditions associated with, or having etiologies involving, vitamin B3 deficiency that may be treated and/or prevented in accordance with the methods described include indigestion, fatigue, canker sores, vomiting, poor circulation, burning in the mouth, swollen red tongue, and depression. Severe vitamin B3 deficiency can cause a condition known as pellagra, a premature aging condition that is characterized by cracked, scaly skin, dementia, and diarrhea. Other conditions characterized by premature or accelerated aging include Cockayne Syndrome, Neill-Dingwall Syndrome, Ataxia-Telangiectasia, progeria, and the like.

In certain embodiments, the present invention provides methods for treating and/or preventing symptoms, diseases, disorders, or conditions selected from, but not limited to, chemical & food dependency, PTSD, chronic stress, depression and anxiety, chronic pain, "chemo-brain," CTE, Parkinson's disease, and Alzheimer's disease, Huntington's disease and various forms of Ataxia, or Long-COVID. In other embodiments, the present methods may be used for athletes and the support of exercise, endurance training, and muscle recovery.

In certain embodiments, the present invention provides methods for treating and/or preventing symptoms, diseases, disorders, or conditions that would benefit from increased mitochondrial activity. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, symptoms, diseases, disorders, or conditions that would benefit from increased mitochondrial activity include symptoms, diseases, disorders, or conditions associated with mitochondrial dysfunction.

In certain embodiments, methods for treating and/or preventing symptoms, diseases, disorders, or conditions that would benefit from increased mitochondrial activity may comprise identifying a subject suffering from a mitochondrial dysfunction. Methods for diagnosing a mitochondrial dysfunction that may involve molecular genetic, pathologic, and/or biochemical analysis are summarized in Bruce H. Cohen & Deborah R. Gold, Mitochondrial cytopathy in adults: what we know so far, 68 CLEVELAND CLINIC J.

MED. 625 (2001). One method for diagnosing a mitochondrial dysfunction is the Thor-Byrneier scale (see, e.g., Cohen & Gold 2001; S. Collins et al., Respiratory Chain Encephalomyopathies: A Diagnostic Classification, 36 EUROPEAN NEUROLOGY 260 (1996)).

Mitochondria are critical for the survival and proper function of almost all types of eukaryotic cells. Mitochondria in virtually any cell type can have congenital or acquired defects that affect their function. Thus, the clinically significant signs and symptoms of mitochondrial defects affecting respiratory chain function are heterogeneous and variable depending on the distribution of defective mitochondria among cells and the severity of their deficits, and upon physiological demands upon the affected cells. Nondividing tissues with high energy requirements, e.g., nervous tissue, skeletal muscle, and cardiac muscle are particularly susceptible to mitochondrial respiratory chain dysfunction, but any organ system can be affected.

Mitochondria are the primary source of free radicals and reactive oxygen species, due to spillover from the mitochondrial respiratory chain, especially when defects in one or more respiratory chain components impairs orderly transfer of electrons from metabolic intermediates to molecular oxygen. To reduce oxidative damage, cells can compensate by expressing mitochondrial uncoupling proteins (UCP), of which several have been identified. UCP-2 is transcribed in response to oxidative damage, inflammatory cytokines, or excess lipid loads, e.g., fatty liver and steatohepatitis. UCPs reduce spillover of reactive oxygen species from mitochondria by discharging proton gradients across the mitochondrial inner membrane, in effect wasting energy produced by metabolism and rendering cells vulnerable to energy stress as a trade-off for reduced oxidative injury.

Symptoms, diseases, disorders, and conditions associated with mitochondrial dysfunction include symptoms, diseases, disorders, and conditions in which deficits in mitochondrial respiratory chain activity contribute to the development of pathophysiology of such symptoms, diseases, disorders, or conditions in a mammal. This includes 1) congenital genetic deficiencies in activity of one or more components of the mitochondrial respiratory chain, wherein such deficiencies are caused by a) oxidative damage during aging; b) elevated intracellular calcium; c) exposure of affected cells to nitric oxide; d) hypoxia or ischemia; c) microtubule-associated deficits in axonal transport of mitochondria; or f) expression of mitochondrial uncoupling proteins.

Symptoms, diseases, disorders, or conditions that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis. Exemplary symptoms, diseases, disorders, or conditions that would benefit from increased mitochondrial activity include, for example, AD (Alzheimer's Disease), ADPD (Alzheimer's Disease and Parkinson's Disease), AMDF (Ataxia, Myoclonus and Deafness), auto-immune disease, lupus, lupus erythematosus, SLE (systemic lupus erythematosus), cataracts, cancer, CIPO (Chronic Intestinal Pseudoobstruction with myopathy and Ophthalmoplegia), congenital muscular dystrophy, CPEO (Chronic Progressive External Ophthalmoplegia), DEAF (Maternally inherited DEAFness or aminoglycoside-induced DEAFness), DEMCHO (Dementia and Chorea), diabetes mellitus (Type I or Type II), DID-MOAD (Diabetes Insipidus, Diabetes Mellitus, Optic Atrophy, Deafness), DMDF (Diabetes Mellitus and Deafness), dystonia, Exercise Intolerance, ESOC (Epilepsy, Strokes, Optic atrophy, and Cognitive decline), FBSN (Familial Bilateral Striatal Necrosis), FICP (Fatal Infantile Cardiomyopathy Plus, a MELAS-associated cardiomyopathy), GER (Gastrointestinal Reflux), HD (Huntington's Disease), KSS (Kearns Sayre Syndrome), "later-onset" myopathy, LDYT (Leber's hereditary optic neuropathy and DYsTonia), Leigh's Syndrome, LHON (Leber Hereditary Optic Neuropathy), LIMM (Lethal Infantile Mitochondrial Myopathy), MDM (Myopathy and Diabetes Mellitus), MELAS (Mitochondrial Encephalomyopathy, Lactic Acidosis, and Stroke-like episodes), MEPR (Myoclonic Epilepsy and Psychomotor Regression), MERME (MERRF/MELAS overlap discasc), MERRF (Myoclonic Epilepsy and Ragged Red Muscle Fibers), MHCM (Maternally Inherited Hypertrophic CardioMyopathy), MICM (Maternally Inherited Cardiomyopathy), MILS (Maternally Inherited Leigh Syndrome), Mitochondrial Encephalocardiomyopathy, Mitochondrial Encephalomyopathy, MM (Mitochondrial Myopathy), MMC (Maternal Myopathy and Cardiomyopathy), MNGIE (Myopathy and external ophthalmoplegia, Neuropathy, Gastro-Intestinal, Encephalopathy), Multisystem Mitochondrial Disorder (myopathy, encephalopathy, blindness, hearing loss, peripheral neuropathy), NARP (Neurogenic muscle weakness, Ataxia, and Retinitis Pigmentosa; alternate phenotype at this locus is reported as Leigh Disease), PD (Parkinson's Disease), Pearson's Syndrome, PEM (Progressive Encephalopathy), PEO (Progressive External Ophthalmoplegia), PME (Progressive Myoclonus Epilepsy), PMPS (Pearson Marrow-Pancreas Syndrome), psoriasis, RTT (Rett Syndrome), schizophrenia, SIDS (Sudden Infant Death Syndrome), SNHL (Sensorineural Hearing Loss), Varied Familial Presentation (clinical manifestations range from spastic paraparesis to multisystem progressive disorder & fatal cardiomyopathy to truncal ataxia, dysarthria, severe hearing loss, mental regression, ptosis, ophthalmoparesis, distal cyclones, and diabetes mellitus), Wolfram syndrome, or Mild Cognitive Impairment and symptoms associated with Long-COVID. Treatments for cardiovascular diseases are contemplated including but not limited to atrial fibrillation, congestive heart failure, reduced right or left ejection fraction, or myocardial infarction.

Other symptoms, diseases, disorders, and conditions that would benefit from increased mitochondrial activity include, for example, Friedreich's ataxia and other ataxias, amyotrophic lateral sclerosis (ALS) and other motor neuron diseases, macular degeneration, epilepsy, Alpers syndrome, Multiple mitochondrial DNA deletion syndrome, MtDNA depletion syndrome, Complex I deficiency, Complex II (SDH) deficiency, Complex III deficiency, Cytochrome c oxidase (COX, Complex IV) deficiency, Complex V deficiency, Adenine Nucleotide Translocator (ANT) deficiency, Pyruvate dehydrogenase (PDH) deficiency, Ethylmalonic aciduria with lactic acidemia, Refractory epilepsy with declines during infection, Asperger syndrome with declines during infection, Autism with declines during infection, Attention deficit hyperactivity disorder (ADHD), Cerebral palsy with declines during infection, Dyslexia with declines during infection, materially inherited thrombocytopenia and leukemia syndrome, MARIAHS syndrome (Mitochondrial ataxia, recurrent infections, aphasia, hypouricemia/hypomyelination, seizures, and dicarboxylic aciduria), ND6 dystonia, Cyclic vomiting syndrome with declines during infection, 3-Hydroxy isobutyric aciduria with lactic acidemia, Diabetes mellitus with lactic acidemia, Uridine responsive neurologic syndrome (URNS), Dilated cardiomyopathy, Splenic Lymphoma, or Renal Tubular Acidosis/Diabetes/Ataxis syndrome.

In other embodiments, the present invention provides intravenous methods for treating a mammal (e.g., human) suffering from mitochondrial disorders arising from, but not limited to, Post-traumatic head injury and cerebral edema, Stroke (invention methods useful for treating or preventing reperfusion injury), Lewy body dementia, Hepatorenal syndrome, Acute liver failure, NASH (non-alcoholic steatohepatitis), Anti-metastasis/prodifferentiation therapy of cancer, Idiopathic congestive heart failure, Atrial fibrillation (non-valvular), Wolff-Parkinson-White Syndrome, Idiopathic heart block, Prevention of reperfusion injury in acute myocardial infarctions, Familial migraines, Irritable bowel syndrome, Secondary prevention of non-Q wave myocardial infarctions, Premenstrual syndrome, Prevention of renal failure in hepatorenal syndrome, Anti-phospholipid antibody syndrome, Eclampsia/pre-eclampsia, Oopause infertility, Ischemic heart disease/Angina, and Shy-Drager and unclassified dysautonomia syndromes. Viral or bacterial infections may be treated.

In still another embodiment, there are provided intravenous methods for the treatment of mitochondrial disorders associated with pharmacological drug-related side effects. Types of pharmaceutical agents that are associated with mitochondrial disorders include reverse transcriptase inhibitors, protease inhibitors, inhibitors of DHOD, antiviral agents, antibiotics, antibacterials, antifungal agents, and the like. Examples of reverse transcriptase inhibitors include, for example, Azidothymidine (AZT), Stavudine (D4T), Zalcitabine (ddC), Didanosine (DDI), Fluoroiodoarauracil (FIAU), Lamivudine (3TC), Abacavir, and the like. Examples of protease inhibitors include, for example, Ritonavir, Indinavir, Saquinavir, Nelfinavir, and the like. Examples of inhibitors of dihydroorotate dehydrogenase (DHOD) include, for example, Leflunomide, Brequinar, and the like. The agents described hereinabove may be combined with NR and/or a nicotinyl compound (I-X) or a derivative, prodrug or salt thereof in an I.V. formulation.

Reverse transcriptase inhibitors not only inhibit reverse transcriptase but also polymerase gamma, which is required for mitochondrial function. Inhibition of polymerase gamma activity (e.g., with a reverse transcriptase inhibitor) therefore leads to mitochondrial dysfunction and/or a reduced mitochondrial mass, which manifests itself in patients as hyperlactatemia. This type of condition may benefit from an increase in the number of mitochondria and/or an improvement in mitochondrial function.

Common symptoms of mitochondrial diseases include cardiomyopathy, muscle weakness and atrophy, developmental delays (involving motor, language, cognitive, or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, migraine, hepatic failure, lactic acidemia, and diabetes mellitus.

In exemplary embodiments, the invention provides methods for treating diseases or disorders that would benefit from increased mitochondrial activity by administering to a mammal (e.g., human) by using I.V. administration a therapeutically effective amount of NR (I) and/or at least one nicotinyl compound (II-X) or a derivative, prodrug or salt thereof alone or in combination with at least one vitamin. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

A gene defect underlying Friedreich's Ataxia (FA), the most common hereditary ataxia, was recently identified and is designated "frataxin." In FA, after a period of normal development, deficits in coordination develop that progress to paralysis and death, typically between the ages of 30 and 40. The tissues affected most severely are the spinal cord, peripheral nerves, myocardium, and pancreas. Patients typically lose motor control and are confined to wheel chairs, and are commonly afflicted with heart failure and diabetes. The genetic basis for FA involves GAA trinucleotide repeats in an intron region of the gene encoding frataxin. The presence of these repeats results in reduced transcription and expression of the gene. Frataxin is involved in regulation of mitochondrial iron content. When cellular frataxin content is subnormal, excess iron accumulates in mitochondria, promoting oxidative damage and consequent mitochondrial degeneration and dysfunction. When intermediate numbers of GAA repeats are present in the frataxin gene intron, the severe clinical phenotype of ataxia may not develop. However, these intermediate-length trinucleotide extensions are found in 25 to 30% of patients with non-insulin dependent diabetes mellitus, compared to about 5% of the nondiabetic population. In certain embodiments, NR (I) and/or at least one nicotinyl compound (II-X) or derivatives, prodrugs, or salts thereof alone or in combination with vitamins may be used for treating mammals (e.g., human) with disorders related to deficiencies or defects in frataxin, including Friedreich's Ataxia, myocardial dysfunction, diabetes mellitus, and complications of diabetes-like peripheral neuropathy.

Muscular dystrophy refers to a family of diseases involving deterioration of neuromuscular structure and function, often resulting in atrophy of skeletal muscle and myocardial dysfunction. In the case of Duchenne muscular dystrophy, mutations or deficits in a specific protein, dystrophin, are implicated in its etiology. Mice with their dystrophin genes inactivated display some characteristics of muscular dystrophy, and have an approximately 50% deficit in mitochondrial respiratory chain activity. A final common pathway for neuromuscular degeneration, in most cases, is calcium-mediated impairment of mitochondrial function. In certain embodiments, NR (I) and/or at least one nicotinyl compound (II-X) or derivatives, prodrugs or salts thereof alone or in combination with vitamins may be used for reducing the rate of decline in muscular functional capacities and for improving muscular functional status in mammals (e.g., human) with muscular dystrophy.

Epilepsy is often present in patients with mitochondrial cytopathies, involving a range of seizure severity and frequency, e.g., absence, tonic, atonic, myoclonic, and status epilepticus, occurring in isolated episodes or many times daily. In certain embodiments, NR (I) and/or at least one nicotinyl compound (II-X) or derivatives, prodrugs or salts thereof alone or in combination with vitamins may be used for treating mammals (e.g., human) with seizures secondary to mitochondrial dysfunction, including reducing frequency and severity of seizure activity.

Delays in neurological or neuropsychological development are often found in children with mitochondrial diseases. Development and remodeling of neural connections requires intensive biosynthetic activity, particularly involving synthesis of neuronal membranes and myelin, both of which require pyrimidine nucleotides as cofactors. Uridine nucleotides are involved in activation and transfer of sugars to glycolipids and glycoproteins. Cytidine nucleotides are derived from uridine nucleotides, and are crucial for synthesis of major membrane phospholipid constituents like phosphatidylcholine, which receives its choline moiety from cytidine diphosphocholine. In the case of mitochondrial dysfunction (due to either mitochondrial DNA defects or any of the acquired or conditional deficits like excitotoxic or nitric oxide-mediated mitochondrial dysfunction) or other conditions resulting in impaired pyrimidine synthesis, cell proliferation and axonal extension are impaired at crucial stages in development of neuronal interconnections and circuits, resulting in delayed or arrested development of neuropsychological functions like language, motor, social, executive function, and cognitive skills. In autism, for example, magnetic resonance spectroscopy measurements of cerebral phosphate compounds indicate that there is global undersynthesis of membranes and membrane precursors indicated by reduced levels of uridine diphosphosugars, and cytidine nucleotide derivatives involved in membrane synthesis. Disorders characterized by developmental delay include Rett's Syndrome, pervasive developmental delay (or PDD-NOS "pervasive developmental delay not otherwise specified" to distinguish it from specific subcategories like autism), autism, Asperger's Syndrome, and Attention Deficit/Hyperactivity Disorder (ADHD), which is becoming recognized as a delay or lag in development of neural circuitry underlying executive functions. In certain embodiments, NR (I) and/or at least one nicotinyl compound (II-X) or derivatives, prodrugs or salts thereof alone or in combination with vitamins may be useful for treating mammals (e.g., human) with neurodevelopmental delays (e.g., involving motor, language, executive function, and cognitive skills), or other delays or arrests of neurological and neuropsychological development in the nervous system and somatic development in non-neural tissues like muscle and endocrine glands.

Oxygen deficiency results in both direct inhibition of mitochondrial respiratory chain activity by depriving cells of a terminal electron acceptor for Cytochrome c reoxidation at Complex IV, and indirectly, especially in the nervous system, via secondary post-anoxic excitotoxicity and nitric oxide formation. In conditions like cerebral anoxia, angina or sickle cell anemia crises, tissues are relatively hypoxic. In such cases, compounds that increase mitochondrial activity provide protection of affected tissues from deleterious effects of hypoxia, attenuate secondary delayed cell death, and accelerate recovery from hypoxic tissue stress and injury. In certain embodiments, NR (I) and/or at least one nicotinyl compound (II-X) or derivatives, prodrugs or salts thereof alone or in combination with vitamins may be useful for treating and/or preventing delayed cell death (apoptosis in regions like the hippocampus or cortex occurring about 2 to 5 days after an episode of cerebral ischemia) after ischemic or hypoxic insult to the brain.

Acidosis due to renal dysfunction is often observed in patients with mitochondrial disease, whether the underlying respiratory chain dysfunction is congenital or induced by ischemia or cytotoxic agents like cisplatin. Renal tubular acidosis often requires administration of exogenous sodium bicarbonate to maintain blood and tissue pH. In certain embodiments, NR (I) and/or at least one nicotinyl compound (II-X) or derivatives, prodrugs or salts thereof alone or in combination with vitamins may be useful for treating and/or preventing renal tubular acidosis and other forms of renal dysfunction caused by mitochondrial respiratory chain deficits.

Mitochondrial DNA damage is more extensive and persists longer than nuclear DNA damage in cells subjected to oxidative stress or cancer chemotherapy agents like cisplatin due to both greater vulnerability and less efficient repair of mitochondrial DNA. Although mitochondrial DNA may be more sensitive to damage than nuclear DNA, it is relatively resistant, in some situations, to mutagenesis by chemical carcinogens. This is because mitochondria respond to some types of mitochondrial DNA damage by destroying their defective genomes rather than attempting to repair them. This results in global mitochondrial dysfunction for a period after cytotoxic chemotherapy. Clinical use of chemotherapy agents like cisplatin, mitomycin, and cytoxan is often accompanied by debilitating "chemotherapy fatigue," prolonged periods of weakness and exercise intolerance that may persist even after recovery from hematologic and gastrointestinal toxicities of such agents. In certain embodiments, NR (I) and/or at least one nicotinyl compound (II-X) or derivatives, prodrugs or salts thereof alone or in combination with vitamins may be useful for treatment and/or prevention of side effects of cancer chemotherapy related to mitochondrial dysfunction.

In certain embodiments, NR (I) and/or at least one nicotinyl compound (II-X) or derivatives, prodrugs or salts thereof alone or in combination with vitamins may be useful for treatment and/or prevention of mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, non-Mendelian inheritance pattern. Mutations in nuclear-encoded mitochondrial enzymes occur.

In certain embodiments, NR (I) and/or at least one nicotinyl compound (II-X) or derivatives, prodrugs or salts thereof alone or in combination with vitamins may be useful for treating patients suffering from toxic damage to mitochondria, such as, toxic damage due to calcium accumulation, excitotoxicity, nitric oxide exposure, drug induced toxic damage, or hypoxia.

A fundamental mechanism of cell injury, especially in excitable tissues, involves excessive calcium entry into cells, as a result of either leakage through the plasma membrane or defects in intracellular calcium handling mechanisms. Mitochondria are major sites of calcium sequestration, and preferentially utilize energy from the respiratory chain for taking up calcium rather than for ATP synthesis, which results in a downward spiral of mitochondrial failure, because calcium uptake into mitochondria results in diminished capabilities for energy transduction.

Excessive stimulation of neurons with excitatory amino acids is a common mechanism of cell death or injury in the central nervous system. Activation of glutamate receptors, especially of the subtype designated NMDA receptors, results in mitochondrial dysfunction, in part through elevation of intracellular calcium during excitotoxic stimulation. Conversely, deficits in mitochondrial respiration and oxidative phosphorylation sensitizes cells to excitotoxic stimuli, resulting in cell death or injury during exposure to levels of excitotoxic neurotransmitters or toxins that would be innocuous to normal cells.

Nitric oxide (about 1 micromolar) inhibits cytochrome oxidase (Complex IV) and thereby inhibits mitochondrial respiration; moreover, prolonged exposure to nitric oxide (NO) irreversibly reduces Complex I activity. Physiological or pathophysiological concentrations of NO thereby inhibit pyrimidine biosynthesis. Nitric oxide is implicated in a variety of neurodegenerative disorders including inflammatory and autoimmune diseases of the central nervous system and is involved in mediation of excitotoxic and post-hypoxic damage to neurons.

Oxygen is the terminal electron acceptor in the respiratory chain. Oxygen deficiency impairs electron transport chain activity, resulting in diminished pyrimidine synthesis as well as diminished ATP synthesis via oxidative phosphorylation. Human cells proliferate and retain viability under virtually anaerobic conditions if provided with uridine and pyruvate (or a similarly effective agent for oxidizing NADH to optimize glycolytic ATP production).

In certain embodiments, nicotinyl compounds (I derivative, II, and/or III) or derivatives, prodrugs or salts thereof alone or in combination with vitamins (IV, V, VI, and/or VII) may be useful for treating and/or preventing diseases or disorders associated with mitochondrial deregulation.

Transcription of mitochondrial DNA encoding respiratory chain components requires nuclear factors. In neuronal axons, mitochondria must shuttle back and forth to the nucleus in order to maintain respiratory chain activity. If axonal transport is impaired by hypoxia or by drugs like taxol that affect microtubule stability, mitochondria distant from the nucleus undergo loss of cytochrome oxidase activity. Accordingly, treatment with NR (I) and/or at least one nicotinyl compound (II-X) or derivatives, prodrugs or salts thereof alone or in combination with vitamins may be useful for promoting nuclear-mitochondrial interactions.

The compositions and methods described in the embodiments above may be further understood in connection with the following Examples. In addition, the following non-limiting examples are provided to illustrate the invention. However, the person skilled in the art will appreciate that it may be necessary to vary the procedures for any given embodiment of the invention, e.g., vary the order or steps of the methods.

Example 1

Exemplary I.V. Formulation Containing NR Chloride (as a Crystalline Component)

NR chloride was obtained from ChromaDex, Inc. (Los Angeles, California).

In an embodiment, the NR chloride as crystalline Form I and/or Form II is available as a lyophilized powder or a crystalline powder prepared as follows, in lots, batches or units of 25 mg to 3 g, inclusive.

In an embodiment, the lyophilized powder (or crystalline powder) is reconstituted in bacteriostatic and sterile, pyrogen-free USP water for dilution with an I.V. fluid for I.V. administration by the standard method. In one example, a batch of 25 mg up to 3 g of NR chloride Form I is added to a bag of normal Saline solution. The resulting I.V. fluid is stored at room temperature (25° C.), or is refrigerated, or is frozen for later use.

Example 2

I.V. Administration of NR Chloride

In an embodiment, NR chloride provided in Example 1 is administered to a human subject (e.g., ca. 70-80 kg male, or 50-70 kg female) by I.V. infusion over about 1 hour. It is expected that the present delivery method will present improved therapeutic delivery characteristics when compared with direct infusion of NAD+ to a similar subject. For example, less burning, chest discomfort, uncomfortable/labored breathing, or other painful sensation is expected during and after infusion of NR chloride compared with NAD+, or other NAD+ containing infusions. Further, NAD+ levels may be measured in serum or tissues using standard methods.

When using a VAS pain scale ('0' to '10' units) assessment the human subject(s) show a significant decrease of several units on the pain scale, or reported no significant pain ('0' to '1' on the VAS pain scale). In a treatment scenario, where subjects exhibit a tingling sensation in the lips, pain may register in the range 1-3, and thus subsequently be lowered upon I.V. treatment.

Example 3

I.V. administration of NR chloride in bacteriostatic and sterile, pyrogen-free USP water for dilution with an I.V. fluid by the standard method as described above is expected to produce increases in serum or tissue NAD+ greater than chronic I.V. administration of NR chloride at higher dose levels of 100-200 mg/kg/day, or greater than oral administration of NR chloride. See, Example 4 and FIG. 3 where the dosage is 500 mg/day.

Example 4

Randomized, placebo-controlled, pilot clinical study evaluating Niagen®+IV (NR IV) and NAD+ IV in healthy adults.

Background

Nicotinamide riboside (NR) is a promising compound for augmenting the intracellular NAD+ pool, potentially mitigating age-related decline and associated conditions. While oral NR supplementation has demonstrated safety and bioavailability in multiple animal and human studies, the effects of intravenous NR (NR IV) are far less understood. Until now, pharmaceutical grade NR was not available for injection research.

Objectives

Given that intravenous administration may offer advantages in certain conditions and contexts, a systematic investigation of the clinical effects of NR IV is warranted.

Methods

The present randomized, double-blinded, placebo-controlled, pilot clinical study was initiated with the primary aim of investigating the safety, tolerability, and the blood NAD+-boosting efficacy of an acute, single dose of NR IV (500 mg, test), NAD+ IV (500 mg, active comparator), oral NR (500 mg, bridge), and saline IV (placebo control) in generally healthy adult participants. The study consisted of two parts; data from 37 and 16 participants in the first and second phases, respectively, were analyzed.

Results

No significant differences in vital signs were detected across groups. In comparison to NAD+ IV, NR IV was associated with fewer and less severe adverse experiences during the infusion; no attributable adverse events were reported through the 14-day follow-up period for any treatment groups. Further, the mean tolerable infusion time for NR IV was 75% less than that of NAD+ IV. No clinically meaningful changes in blood chemistry markers were described in the NR IV condition, whereas an increase in white blood cell counts and neutrophils was observed in the NAD+ IV condition, suggesting the presence of an inflammatory response. Finally, NR IV appeared to promote the most robust increases in NAD+ concentration as measured by dried blood spot analyses, with peak NAD+ levels increasing by 20.7% relative to baseline, and acutely outperforming NAD+ IV ($p<0.01$) and oral NR ($p<0.01$) at the 3-hr timepoint. See, e.g., FIGS. 3-7.

Conclusions

This is the first study to clinically evaluate NR IV. Overall, acute intravenous infusions of 500 mg NR were safe in the study participants with no attributable adverse events and only minor and transient infusion-related experiences. In comparison to NAD+ IV, NR IV had a faster infusion time with superior tolerability. At 3 hours post-infusion, blood NAD+ levels were significantly higher in the NR IV group compared to the NAD+ IV group.

Introductory Information

While NAD+ is commercially available as dietary supplement and intravenous drug products, as a pyridine nucleotide, NAD+ itself is unable to undergo direct intestinal absorption or cellular uptake intact upon exogenous administration (Nikiforov et al., Pathways and Subcellular Compartmentation of NAD Biosynthesis in Human Cells. *J Biol Chem* (2011) 286:21767-21778). The majority of NAD+ is instead hydrolyzed in the extracellular environment to nicotinamide mononucleotide (NMN), which in turn is further cleaved by CD73 to form nicotinamide riboside (NR), a portion of which may be further degraded to nicotinamide and nicotinic acid (Nikiforov et al., 2011; Anthony A. Sauve et al., Triple-Isotope Tracing for Pathway Discernment of NMN-Induced NAD+ Biosynthesis in Whole Mice. *Int J Mol Sci* (2023) 24:11114). NR is readily taken up by cells via equilibrative nucleoside transporters and directed toward NAD+ biosynthesis in a two-step process involving the nicotinamide riboside kinase enzymes (Bieganowski and Brenner, Discoveries of Nicotinamide Riboside as a Nutrient and Conserved NRK Genes Establish a Preiss-Handler Independent Route to NAD+ in Fungi and Humans. Cell (2004) 117:495-502; Nikiforov et al., 2011; Ratajczak et al., NRKI controls nicotinamide mononucleotide and nicotinamide riboside metabolism in mammalian cells. *Nat Commun* (2016) 7:13103; Kropotov et al., Equilibrative Nucleoside Transporters Mediate the Import of Nicotinamide Riboside and Nicotinic Acid Riboside into Human Cells. *Int J Mol Sci* (2021) 22:1391). Therefore, the provision of exogenous NR, rather than NAD+ itself, appears to be more efficient for augmenting intracellular NAD+ concentrations. Indeed, oral NR administration has been described to be safe and effective in raising NAD+ and has shown promise against neurodegenerative conditions and other age-related disorders (Samuel A. J. Trammell et al., Nicotinamide riboside is uniquely and orally bioavailable in mice and humans. *Nat Commun* (2016) 7:12948; Elhassan et al., Nicotinamide Riboside Augments the Aged Human Skeletal Muscle NAD+ Metabolome and Induces Transcriptomic and Anti-inflammatory Signatures. Cell Rep (2019) 28:1717-1728.c6; Brakedal et al., The NADPARK study: A randomized phase I trial of nicotinamide riboside supplementation in Parkinson's disease. *Cell Metab* (2022) 34:396-407.c6; Berven et al., NR-SAFE: a randomized, double-blind safety trial of high dose nicotinamide riboside in Parkinson's disease. *Nat Commun* (2023) 14:7793; Biţă et al., *Nicotinamide Riboside, a Promising Vitamin B*3 *Derivative for* Healthy Aging and Longevity: Current Research and Perspectives. *Molecules* (2023) 28:6078). Other notable NAD+ precursors include NRH and NMNH known for significantly augmenting NAD+ and NADH levels. (Rubén Zapata-Pérez et al., Reduced nicotinamide mononucleotide is a new and potent NAD+ precursor in mammalian cells and mice. *The Faseb Journal* (2021) 35: c21456. Judith Giroud-Gerbetant et al., A reduced form of nicotinamide riboside defines a new path for NAD+ biosynthesis and acts as an orally bioavailable NAD+ precursor. Mol Metab. (2019) 30:192-202.

In spite of the aforementioned limitations concerning the provision of exogenous NAD+, the intravenous (IV) administration of NAD+ ('NAD+ IV') has gained popularity in recent years and is available in thousands of boutique medical and hydration clinics globally. Initially described in the clinical literature in 1961 for use in the treatment of multiple addictions (O'Hollaren, Diphosphopyridine Nucleotide in the Prevention, Diagnosis and Treatment of Drug Addiction, *West J. Surg., Obst. & Gynec.* May-June 1961, pp. 1-2), NAD+ infusion therapy is now widely used for the promotion of overall well-being and longevity. Purported benefits of NAD+IV include, but are not limited to, depression and anxiety reduction, drug and alcohol addiction treatment, hangover relief, fatigue, neurological disorders, athletic performance, and most recently, recovery from symptoms of COVID-19 and post-acute sequelae of SARS-COV-2 infection (PASC, 'long-COVID'). Intravenous infusions may be preferred to oral administration under certain clinical circumstances, as direct delivery into the bloodstream can provide 100% bioavailability, which is not achieved through oral supplementation. Nevertheless, despite the wide availability and a broad range of anecdotally reported benefits of NAD+ IV, there is a paucity of human data interrogating its use as a treatment or health-modifying modality.

Aside from the metabolic inefficiency associated with direct exogenous NAD+ administration (via oral, IV, or intramuscular routes) due to the requisite need for its breakdown into its constituent pyridine metabolites before cellular entry, raising extracellular NAD+ (eNAD+) may also provoke maladaptive effects. Under normal physiological conditions, NAD+ is reported to circulate in mammalian extracellular fluids in concentrations between 0.1 and 0.5 μM (Adriouch et al., Extracellular NAD+: a danger signal hindering regulatory T cells. *Microbes Infect* (2012) 14:1284-1292; Gasparrini et al., Enzymology of extracellular NAD metabolism. *Cell Mol Life Sci* (2021) 78:3317-3331). Increased eNAD+ beyond homeostatic-controlled ranges may represent a pathophysiological trigger, resulting in pro-inflammatory signaling, toxic effects on T-cells in preclinical models, including apoptosis (Adriouch et al., Rapid Induction of Naive T Cell Apoptosis by Ecto-Nicotinamide Adenine Dinucleotide: Requirement for Mono (ADP-Ribosyl) Transferase 2 and a Downstream Effector. *J Immunol* (2001) 167:196-203; Liu et al., Extracellular Nicotinamide Adenine Dinucleotide Induces T Cell Apoptosis In Vivo and In Vitro. *J Immunol* (2001) 167:4942-4947), and potentially suppressing immune responses (Liu et al., 2001). These findings highlight the need for caution with NAD+ IV, due to its ability to augment eNAD+ to supraphysiologic, potentially pathophysiologic, amounts. Alarmingly, systematic investigations addressing the safety and tolerability of NAD+ IV remain limited despite its widespread use. Clinician- and participant-reported adverse experiences include nausea, diarrhea, muscle cramping, chest pains, and dizziness.

In light of these concerns, the clinical investigation of alternative strategies for boosting NAD through the intravenous route of administration is warranted. Since its recognition as an endogenous form of vitamin B3, as an NAD precursor, nicotinamide riboside (NR) has been the topic of investigation in numerous preclinical and clinical studies (Cantó et al., The NAD+ Precursor Nicotinamide Riboside Enhances Oxidative Metabolism and Protects against High-Fat Dict-Induced Obesity. *Cell Metab* (2012) 15:838-847; Samuel A. J. Trammell et al., 2016; Airhart et al., An open-label, non-randomized study of the pharmacokinetics of the nutritional supplement nicotinamide riboside (NR) and its effects on blood NAD+ levels in healthy volunteers. *PLOS ONE* (2017) 12: c0186459; Martens et al., Chronic nicotinamide riboside supplementation is well-tolerated and elevates $NAD^+$ in healthy middle-aged and older adults. *Nat Commun* (2018) 9:1286; Conze et al., Safety and Metabolism of Long-term Administration of NIAGEN (Nicotinamide Riboside Chloride) in a Randomized, Double-Blind, Placebo-controlled Clinical Trial of Healthy Overweight Adults. *Sci Rep* (2019) 9:9772; Elhassan et al., 2019; Brakedal et al., 2022; Wu et al., Boosting NAD+ blunts toll-like receptor-4 induced type-I interferon in control and systemic lupus erythematosus monocytes. *J Clin Invest* (2022) 132: c139828). Moreover, the patented form of NR chloride, Niagen®, has received favorable safety reviews from multiple regulatory agencies, including the U.S. Food and Drug Administration (FDA), from which it achieved new dietary ingredient and generally recognized as safe (GRAS) status for use in dietary supplement and food products. Although oral Niagen® supplementation has consistently demonstrated safety and efficacy in dose-dependently augmenting cellular NAD+ levels in human intervention studies at doses up to 3,000 mg/day (Conze et al., 2019; Berven et al., 2023), its effects following IV administration have yet to be systematically evaluated. Arguably, by bypassing possible gastrointestinal digestive enzyme- and microbiota-mediated degradation and hepatic first-pass metabolism, administering NR intravenously may exert a more potent impact on systemic $NAD^+$ levels in comparison to oral consumption. Additionally, multiple lines of evidence and mechanistic understandings support the premise that intravenous NR ('NR IV') offers superior safety and NAD-boosting efficiency over NAD+ IV. Since December 2022, NR chloride has been included on the Bulk Drug Substances Category 1 list under evaluation by FDA as an injectable compound under Section 503B of the Federal Food, Drug, and Cosmetic Act (FDA, 2023).

The aim of the present pilot clinical study is to compare the effects of a single intravenous administration of NAD+, NR, or saline vehicle control, and oral NR supplementation on changes in vitals during and after administration, changes in whole blood NAD+, and tolerable infusion rates. Secondary aims are to compare the clinical chemistry safety profiles of the two approaches of IV supplementation and to identify consumer preferences.

Methods

Ethics and Regulatory Authorization

The study was conducted in accordance with the Declaration of Helsinki and adhered to Good Clinical Practice guidelines. The clinical trial was administered by Nutraceuticals Research Institute at Hopewell Family Care (Hermitage, TN) and received full authorization from Sterling IRB (Protocol Number 23-08-0010), an independent ethics review board which is registered with the National Institutes of Health's Office for Human Research Protections (OHRP). This authorization remained in effect through the trial and was expanded to include the addition of study 2. The trial was also registered at ClinicalTrials.gov, NCT06382688. All participants provided written informed consent prior to any intervention procedures.

Trial Design

This was a 2-part study. The first study was a 4-arm randomized, placebo-controlled parallel trial. The 3 IV arms were double-blinded, while the 4th arm involved oral administration making it naturally unblinded. Participants were randomized at a 10:10:10:6 ratio to intravenous placebo (saline), $NAD^+$, NR, or oral NR (oral). The second study was a randomized parallel design trial with two arms for the purpose of evaluating the actual differences in infusion rates in real time. Participants were randomized at a 1:1 ratio to intravenous NR or $NAD^+$.

Participants

Participants were determined to be eligible for this study if they met the following inclusion criteria: Signed and dated the informed consent form, demonstrated ability to comply with study procedures, live within 100 miles of the Nutraceuticals Research Institute (Franklin, TN) study sites, were 40+ years in age, overall good general health, and females with reproductive potential must have used a highly effective contraception for at least 1 month prior to screening as well as agreeing to use such method during study participation and 1 month after the study end date. Study one was open to any sex; study two was restricted to biological males.

Participants were not eligible for either study if they met any of the following exclusion criteria: Current diagnosis of any seizure disorder, diabetes or insulin resistance, any kidney or liver disorder, heart disease, cancer, or Parkinson's Disease, pregnancy, trying to conceive, or breastfeeding, and had any known allergies to any components of the interventions.

Sample Size (1 P)

The purpose of this study was to identify the continuity and variations between the two approaches to IV administration, to serve as a pilot study to collect data for future research, and to provide data for future powered studies.

A post-hoc power analysis was conducted using G*Power to identify the power of the study. Using the findings from the first study tolerable infusion rate on four groups, with an effect size (F) of 10.12 and a p-value of <. 001, the actual power of the study was found to be 99%.

Randomization and Blinding

Participants were adaptively randomized by age and sex using the method developed by Kang et al., Issues in outcomes research: an overview of randomization techniques for clinical trials, *J. Athl. Train.* (2008) 43 (2): 215-211. This ensured even distribution of patients in all groups based on these potentially confounding variables.

Participants and participant-facing study staff were blinded to allocation of interventions, with the exception of the oral group which was naturally unblinded. To maintain blinding, participants were seated in comfortable chairs for IV administration and the IVs were prepared in a different area, out of sight of the participants. The IVs were labeled with the participant's ID.

Intervention

The test intervention for both studies was pharmaceutical grade NR chloride (Niagen®), which was obtained from W. R. Grace (South Haven, MI) for preparation from a compounding pharmacy. The first study, which had a total of four groups, included comparison groups of placebo (saline IV), an active comparator ($NAD^+$), and oral administration of NR chloride. The second study, which had a total of two groups, included the test intervention and active comparator.

Vials of 50 mg/ml of NR or NAD+ were prepared in 10 ml of sterile water by DCA Pharmacy (Franklin, Tennessee) by prescription, for research administration only, and maintained in refrigerated conditions until use. For participants who were randomized to the test group or to the active comparator group, the NR or NAD+ was added to 500 ml of normal saline (B Braun 0.9% sodium chloride injection USP, preservative free) prior to intravenous administration. Those randomly assigned to the saline group received 500 ml of normal saline. Participants that were randomly assigned to the oral arm were provided with 500 mg of NR which was taken with water.

In the first study, participants began the infusion at a rate of 20 drops per minute for the first 15 minutes to ensure safety and comfort. After this initial timepoint, participant input was used to increase or decrease the infusion rate in order to meet or maintain the comfort of the participants throughout the duration of the infusion. In the second study, all participants began with the IV line fully open. Participants were closely monitored for the duration of the infusion, and the infusion rate was decreased, as applicable, upon participant request.

Consented participants were instructed to fast for at least 8 hours prior to the time of the infusion and for at least 8 hours prior to the 24-hour assessments (Study 1 only), consuming only water, black coffee, or black tea. In the event of anticipated side effects, such as nausea, upset stomach, or vomiting, participants were offered saltine crackers and ginger during and after the infusions. Participants were provided a standardized lunch (Study 1) after the administration of the test material.

Outcomes

The safety of the IV infusion was evaluated using a combination of endpoints, including tolerable infusion rate, total number of adverse effects, participant vital signs, a complete blood count (CBC), a comprehensive metabolic panel (CMP), glucose and insulin levels, and the participant's self-reported subjective experience.

Socioeconomic status control variables included age, race, height, weight, BMI, household income, educational attainment, marital status, and employment status.

Adverse event monitoring began on the first day of the study and continued for 14 days (study one) or 7 days (study two). Participants were instructed to notify the research staff of any new or unusual symptoms during the trial and open-ended questions during data collection solicited unexpected side effects.

NAD+ Analysis

Finger punctures were conducted using a lancet. Blood was then applied to the circles on the dried blood spot (DBS) card and allowed to dry for a minimum of 3 hours. Dried cards were stored at −20° C. until shipment for analysis by LC/MS. See, for example, FIG. 3.

Statistical Methods

Continuous demographics and randomization success were assessed using two-sample t-tests. Categorical demographic and randomization variables were assessed using chi-square analysis.

Between-groups comparisons of each outcome measured in the CMC and CMP were evaluated using mixed between-within subjects ANOVA with the timepoint being the within subjects' factor and the group assignment as the between subjects factor. Mauchly's test of sphericity was used to confirm assumptions. Violations of the assumption of sphericity are addressed with the Greenhouse-Geisser correction.

To assess vital signs and subdomains on the sleep and energy scales, between-groups comparisons were assessed using analysis of covariance (ANCOVA) with baseline scores as the covariate and a Bonferroni correction. Levene's test was used to check and confirm the assumption of homogeneity of variances.

Sleep & Energy Results

Tables A-D below reflect mean scores for each group at days 7 and 14. An ANCOVA was used to identify statistical significant differences, using baseline scores as the covariate which helps to account for the natural variation in psychological measurements, increasing the power of the study.

For the energy scale, the greatest improvements at day 7 are those on the mental energy domain and the subjective domain measuring the patient's perceived level of fatigue. By day 14, motivational energy was identified as the greatest improvement. Due to the small sample size, these datapoints are not significant; larger studies would allow for identification of statistical significance.

TABLE A

Energy/Fatigue Scale Day 7

| Test Group | Measurement (row) | | | | |
|---|---|---|---|---|---|
| (coln) | NAD+ | NR-IV | Saline | NR-Oral | p-value |
| Physical Energy | 19.63 | 18.00 | 16.20 | 19.80 | .364 |
| Mental Energy | 13.13 | 10.63 | 10.60 | 14.90 | .716 |
| Emotional Energy | 31.75 | 36.63 | 34.60 | 32.50 | .785 |
| General Energy | 20.63 | 22.75 | 23.60 | 23.20 | .087 |
| Motivation | 11.13 | 10.88 | 10.40 | 12.20 | .675 |
| Perceived Fatigue | 15.75 | 14.75 | 14.20 | 14.10 | .490 |

* Range of possible scores: Physical 7-42/Mental: 5-30/Emotional: 8-48/General: 6-36/Motivation 6-36/erceived Fatigue: 5-30.

TABLE B

Energy/Fatigue Scale Day 14

| Test Group | Measurement (row) | | | | |
|---|---|---|---|---|---|
| (coln) | NAD+ | NR-IV | Saline | NR-Oral | p-value |
| Physical Energy | 18.50 | 20.22 | 16.50 | 20.00 | .973 |
| Mental Energy | 14.50 | 12.33 | 11.33 | 15.67 | .924 |
| Emotional Energy | 29.63 | 36.11 | 35.67 | 32.44 | .478 |
| General Energy | 20.13 | 24.67 | 25.17 | 23.67 | .131 |

TABLE B-continued

| Energy/Fatigue Scale Day 14 | | | | | |
|---|---|---|---|---|---|
| Test Group | Measurement (row) | | | | |
| (coln) | NAD+ | NR-IV | Saline | NR-Oral | p-value |
| Motivation | 13.50 | 11.00 | 12.17 | 12.56 | .411 |
| Perceived Fatigue | 15.50 | 13.22 | 13.00 | 16.44 | .208 |

* Range of possible scores: Physical 7-42/Mental: 5-30/Emotional: 8-48/General: 6-36/ Motivation 6-36/Perceived Fatigue: 5-30.

It is noted that the energy scale measures disruptions to energy levels; lower scores reflect greater levels of energy.

For the sleep scale, the greatest improvements were seen on the scale of sleep latency, which refers to the ability to fall asleep at night, and sleep-related cognitive effects.

TABLE C

| Sleep Scale Day 7 | | | | | |
|---|---|---|---|---|---|
| Test Group | Measurement (row) | | | | |
| (coln) | NAD+ | (coln) | NAD+ | (coln) | NAD+ |
| Daytime Sleepiness | 17.63 | 15.25 | 14.80 | 15.44 | .844 |
| Sleep Inertia | 17.38 | 14.38 | 13.80 | 17.11 | .568 |
| Sleep Latency | 11.63 | 8.25 | 8.60 | 14.44 | .070 |
| Sleep Maintenance | 8.88 | 9.50 | 4.80 | 5.90 | .024** |
| Productivity | 13.86 | 12.50 | 11.60 | 13.78 | .575 |
| Emotional Effects | 15.75 | 21.25 | 20.80 | 18.56 | .778 |
| Cognitive Effects | 15.50 | 13.13 | 11.60 | 18.22 | .725 |

* Range of possible scores: Daytime Sleepiness: 5-30/Sleep Inertia: 5-30/Sleep Latency: 4-24/Sleep Maintenance: 3-18/Productivity: 5-30/Emotional Effects: 5-30/Cognitive Effects: 5-30

**This is not significant after a Bonferroni correction. The significant difference was found in the saline group.

TABLE D

| Sleep Scale Day 14 | | | | | |
|---|---|---|---|---|---|
| Test Group | Measurement (row) | | | | |
| (coln) | NAD+ | NR-IV | Saline | NR-Oral | p-value |
| Daytime Sleepiness | 16.88 | 16.56 | 16.00 | 15.63 | .682 |
| Sleep Inertia | 16.00 | 15.44 | 16.67 | 15.88 | .401 |
| Sleep Latency | 10.75 | 9.00 | 10.17 | 10.00 | .416 |
| Sleep Maintenance | 8.25 | 8.33 | 6.33 | 7.50 | .704 |

TABLE D-continued

| Sleep Scale Day 14 | | | | | |
|---|---|---|---|---|---|
| Test Group | Measurement (row) | | | | |
| (coln) | NAD+ | NR-IV | Saline | NR-Oral | p-value |
| Productivity | 13.25 | 13.56 | 12.67 | 12.88 | .377 |
| Emotional Effects | 16.38 | 21.00 | 20.67 | 20.50 | .184 |
| Cognitive Effects | 15.63 | 15.11 | 12.17 | 16.36 | .291 |

* Range of possible scores: Daytime Sleepiness: 5-30/Sleep Inertia: 5-30/Sleep Latency: 4-24/Sleep Maintenance: 3-18/Productivity: 5-30/Emotional Effects: 5-30/Cognitive Effects: 5-30

Participants were analyzed using an intent-to-treat (ITT) analysis. Those who were randomized to a group and began the study were evaluated in the statistical analysis. All data were analyzed using STATA v17.

Additional Analyses

Additional analyses were conducted using GraphPad Prism (Ver. 10.0.2). Statistical significance was determined as $p<0.05$, with comparisons of the test articles compared to saline or between group comparisons. 2way ANOVA with Tukey's multiple comparisons test with a single pooled variance was used to determine significance in hematology, clinical chemistry, and vitals. Time in chair was analyzed for study 1 by a one-way ANOVA with multiple comparisons, study 2 was analyzed by unpaired t-test. The baseline variable of age was analyzed for differences by one way ANOVA with multiple comparisons for study.

Results

Participant Flow

A total of 45 individuals were assessed for the first study. Of these participants, 2 did not provide consent, and a total of 43 qualified and provided informed consent. Of these, 6 withdrew due to scheduling conflicts. A total of 37 were randomized into one of the four groups and received the intervention, NAD+ IV (n=10); NR IV (n=11); saline (n=6); oral NR (n=10). For the second study, a total of 22 individuals were assessed; 16 qualified and provided informed consent, were randomized to a group, and received an intervention; NAD+ IV (n=8); NR IV (n=8). No participants were removed from the study or withdrew from either study once the trial began. All participants in both studies provided written informed consent prior to any intervention related procedures. Participants were followed until 14 days (first study) or 7 days (second study) after the trial for reporting of adverse events.

Baseline Subject Data

Baseline descriptive statistics were evaluated, and t-tests were performed to ensure balance between each group. No differences between the two groups were identified, indicating that randomization successfully balanced the groups on known factors. In the first study, participants were mostly white (89%) and 41 years old (27%). Gender was indicated by their sex assigned at birth. The gender ratio for this study consisted of 59% male and 41% female. In the second study, all participants were male, with an average age of 45.57 years (range: 40-64). Health history was also similar between groups. There were no differences between groups on any of the baseline control variables. However, these results should be interpreted with caution due to the small sample sizes, as shown in Table 1. Note that both Study 1 and Study 2 are summarized.

TABLE 1

Study 1 and 2 Participant Demographics & Baseline Vitals

| | | Results (Mean ± SD) | | | |
|---|---|---|---|---|---|
| Study | Characteristic | NAD+ IV | NR IV | Saline | Oral |
| Study 1 | Sex (M/F) | 7/3 | 7/4 | 3/3 | 5/5 |
| | Age Mean years (min, max) | 41.60 (40, 46) | 41.50 (40, 45) | 44.00 (40, 51) | 44.20 (40, 48) |
| | Race | White: 7 Hispanic/Latino: 2 Black/African-American: 1 | White: 11 | White: 6 | White: 9 Filipino: 1 |
| | BMI | 25.55 ± 5.38 | 25.35 ± 3.01 | 28.60 ± 4.71 | 26.90 ± 3.02 |
| | Baseline Systolic BP | 118.2 ± 12.57 | 120.7 ± 16.51 | 121.5 ± 14.50 | 113.8 ± 12.40 |
| | Baseline Diastolic BP | 78.60 ± 12.66 | 75.27 ± 10.86$^{\infty}$ | 74.17 ± 9.020 | 73.11 ± 8.796$^{\infty}$ |
| | Baseline Pulse | 73.00 ± 7.513 | 68.09 ± 11.58 | 77.67 ± 12.69 | 66.44 ± 9.126* |
| Study 2 | Sex (M/F) | 8/0 | 8/0 | N/A | N/A |
| | Age Mean years (min, max) | 47.29 (41, 64) | 43.88 (40, 52) | N/A | N/A |
| | Race | White: 7 Other: 1 | White: 6 Other: 2 | N/A | N/A |

$^{\infty}$indicates between group significance.

*indicates significance compared to saline. ANOVA $p < 0.05$

Intent to Treat

For the first study, data from 37 patients were available for intent to treat analysis; for the second study, data from 16 patients were available for intent to treat analysis. Table 2 describes the timepoints for the various assessments that were conducted.

TABLE 2

Study Design

| Study | Procedures | Day 0 | Day 1 Baseline | Day 1 Post Infusion (±10 minutes) | Day 1 3 hr Post Infusion (±15 min) | Day 1 6 hr Post Infusion (±45 min) | Day 2 24 hr Post Infusion (±3 hours) | Day 7 (±1 day) | Day 14 (±1 day) |
|---|---|---|---|---|---|---|---|---|---|
| Study 1 | Screening | X | | | | | | | |
| | Informed Consent | X | X | | | | | | |
| | Demographics & Randomization | X | | | | | | | |
| | Administer IV Infusion/ Oral NR | | X | | | | | | |
| | Vitals | | X | X | X | X | X | | |
| | Blood Draw (CMP, CBC, hematology) | | X | | X | | X | | |
| | Dried Blood Spot Collection | | X | X | X | X | X | | |
| | Subjective Experience | | | X | X | X | X | X | X |
| | Adverse event reporting | | X | X | X | X | X | X | X |
| Study 2 | Screening | X | | | | | | | |
| | Informed Consent | X | X | | | | | | |
| | Demographics & Randomization | X | | | | | | | |
| | Administer IV Infusion/ Oral NR | | X | | | | | | |
| | Vitals | | X | X | | | | | |
| | Subjective Experience | | | X | | | | | |
| | Adverse event review and evaluation | | X | X | | | | X | |

Vital Signs

Post-intervention systolic blood pressure (mmHg) values were 117.20 (SD: 14.54), 121.40 (SD: 13.84, 115.50 (SD: 4.23), and 108.56 (SD: 9.08) in the NAD$^+$ IV, NR IV, saline, and oral groups, respectively. An ANCOVA with baseline systolic blood pressure as the covariate revealed there were no significant changes between groups on scores (F (1,34)=0.22, p=0.882).

Post-intervention diastolic blood pressure (mmHg) values were 73.40 (SD: 13.15), 79.60 (SD: 6.24), 74.83 (SD: 6.59), and 71.00 (SD: 6.24) in the NAD$^+$ IV, NR IV, saline, and oral groups, respectively. An ANCOVA with baseline systolic blood pressure as the covariate revealed there were no significant changes between groups on scores (F (1,34)=1.61, p=0.21).

Post-intervention heart rate (beats per minute, BPM) values were 68.40 (SD: 8.10), 63.45 (SD: 9.42), 65.83 (SD:

12.69), and 65.78 (SD: 7.95) in the NAD$^+$ IV, NR IV, saline, and oral groups, respectively. An ANCOVA with baseline systolic blood pressure as the covariate revealed there were no significant changes between groups on scores (F (1,34) =2.15, p=0.143).

Tolerable Infusion Rates

Figure 2A:
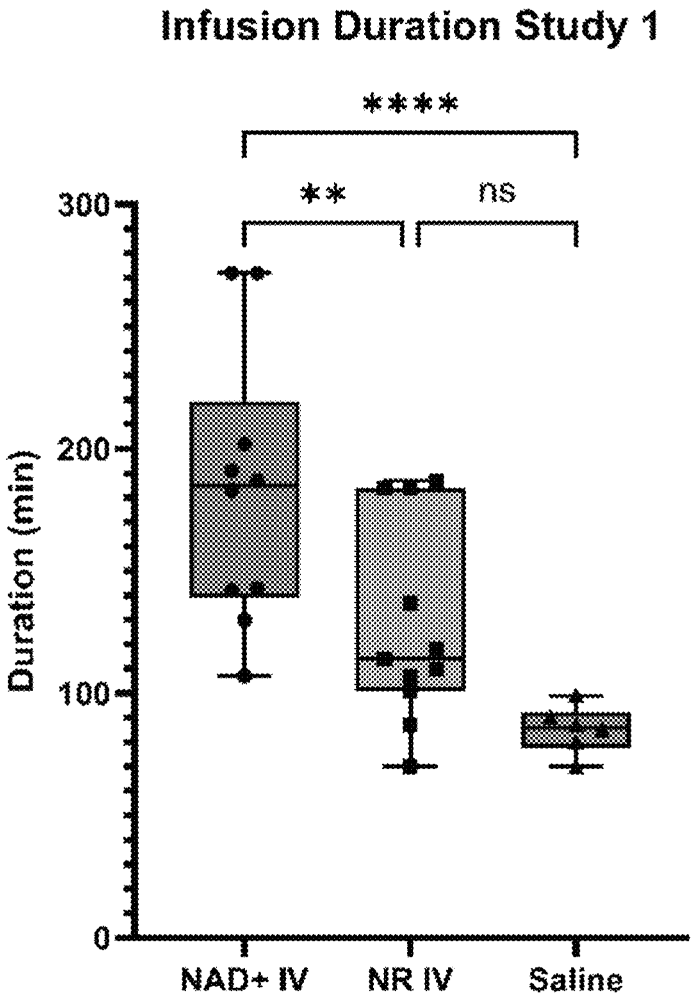
FIG. 2A depicts Study 1 of Infusion duration for $NAD^+$ IV, NR IV, and Saline IV. Infusion duration of Study 1 is shown in minutes, line at the median and whiskers to the minimum and maximum values. Analysis by ANOVA; ns—not significant *p<0.05, p<0.01, **p<0.0001.

In the first study, NR IV infusion intake varied from 1 hour 10 minutes to 3 hours 7 minutes, with the average being 2 hours and 7 minutes (127.2±40.82 minutes). In contrast, the NAD+ IV infusion intake varied from 1 hour and 47 minutes to 4 hours 32 minutes, with the average being 3 hours and 3 minutes (182.9±55.93 minutes). The saline group ranged from 1 hour and 10 minutes to 1 hour and 39 minutes, with the average being 1 hour and 25 minutes (85.17±9.745 minutes). A one-way analysis of variance identified a significant difference between groups (F (1,26) =10.12, p=<. 001). A Bonferroni post-hoc test identified significant differences between the NAD+ IV and NR groups (t=−2.94, p=0.022) and between the NAD+ IV and saline groups (t=−4.36, p=0.001). The effect size, calculated as partial eta squared, was 0.457, which far exceeds the classification of large described by Cohen, et al. (Cohen, J. (1988). Statistical power analysis for the behavioral sciences (2nd ed.). Hillsdale, NJ: Erlbaum. Cohen, J., & Cohen, P. (1983). Applied multiple regression/correlation analysis for the behavioral sciences (2nd ed.). Hillsdale, NJ: Erlbaum). See, FIG. 2A.

Figure 2B:
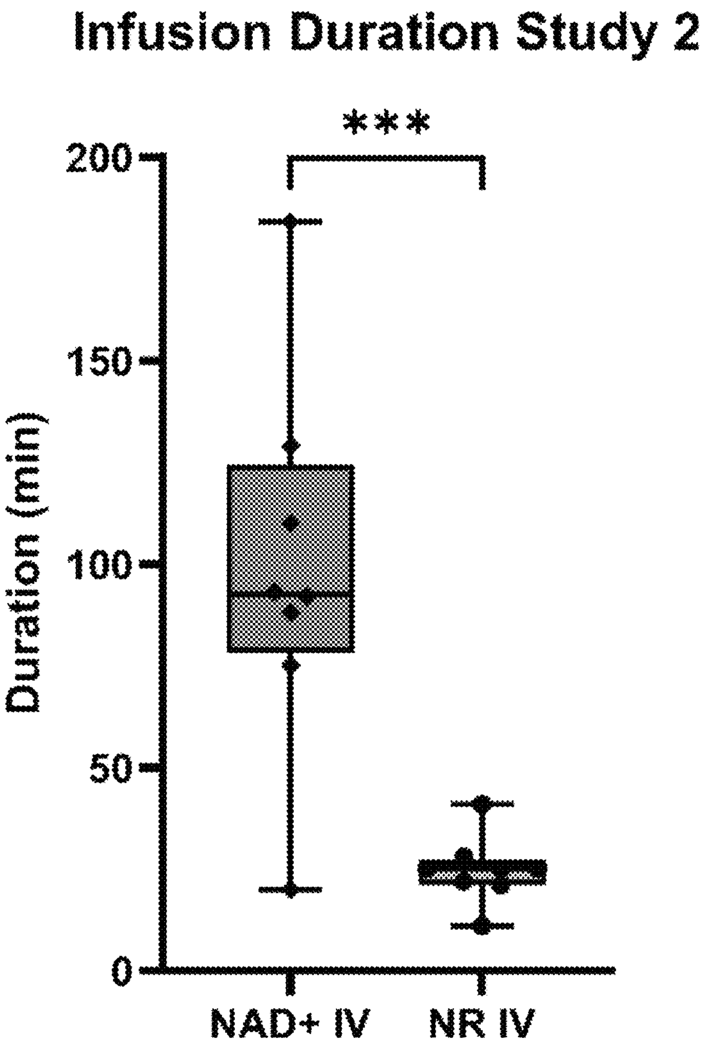
FIG. 2B depicts Study 2 of Infusion duration for $NAD^+$ IV, NR IV. Infusion duration of Study 2 is shown in minutes, line at the median and whiskers to the minimum and maximum values. Analysis by ANOVA; ***p<0.001.

To further elucidate the variation in total infusion time between NR IV and NAD+IV, in the second study an additional 16 male patients received an IV injection of each substance at a 1:1 ratio (n=16). NR IV infusions ranged from 11 minutes to 41 minutes, while NAD+ IV infusions ranged from 20 minutes to 184 minutes. The average infusion rate for NR IV was 24.75 (SD: 8.33) minutes, compared to an average infusion rate for NAD+ IV of 98.88 (SD: 46.70) minutes. A two-tailed t-test was used to compare the differences and revealed that the NR IV infusion rate was significantly and substantially lower than the NAD+ IV infusion rate (t (14)=−4.42, p=<. 001), resulting in a 75% decrease in total time required for NR IV compared to NAD+IV. See, FIG. 2B.

Patient Subjective Experience

Among the NR IV patients, the most commonly reported sensation was tingling in the mouth and in the extremities, e.g. nerve tingling. This was described by patients as "tingly," "slightly painful," "burning," and "weird." One described the feeling "like eating pop rocks." Patients also reported feeling a sensation of pressure in the head and cars to the nursing staff. They described it as feeling congested and during the IV had a "runny nose" at times.

By contrast, the majority of NAD$^+$ IV patients described their comfort level as "low." They self-reported anxiety, headaches, nausea, and sudden urges to have a bowel movement or diarrhea. They described it as feeling "chest tightness and a little woozy," "hot flashes," "feeling queasy," and "cramping in my stomach."

Nursing staff reported additional symptom descriptors of general discomfort or gastrointestinal (GI) discomfort/upset including "feeling gassy," "muscle weakness," "unsettled stomach," and "stomach cramping." Approximately half of the patients receiving NAD$^+$ IV had a bowel movement during the IV.

Clinical Chemistry

Blood chemistry remained relatively stable during the intervention period. A mixed between-within subjects analysis of variance was conducted to assess potential variations between groups and timepoints. While some significant timepoint effects were observed, no significant between groups effects were observed on the endpoints obtained in the CMC and CMP tests. Significant between-groups differences were identified for the outcomes of glucose and insulin.

For the outcome of glucose, the overall model was significant (Wald $\chi^2$ (11, n=37)=41.76, p=<. 001). Post hoc tests identified significant differences between the NAD$^+$ IV group and the saline group ($\chi^2$=7.61; p=0.022) and the oral group ($\chi^2$=18.42; p=<0.001). For the outcome of insulin, the overall model was significant (Wald $\chi^2$ (11, n=37)=56.30, p=<0.001), but there were no significant between-groups differences identified.

Additional Analyses

While there were statistically significant differences between saline, the test group (NR IV) and active comparator group (NAD+ IV), the changes were not deemed clinically significant. An ANOVA analysis indicated a significant difference for NAD+ IV and NR IV to saline in the estimated glomerular filtration rate change from baseline to 3 hours post infusion (NAD+ IV: 1.400±8.462; p=0.0341, NR IV: 1.273±4.941; p=0.0330, Saline: −8.500±12.91). This change was not deemed clinically significant. The change in globulin from baseline to 24 hours post infusion was significantly different in NAD+ IV compared to saline (0.1300±0.1829 and −0.1167±0.2137 respectively; p=0.0418).

An ANOVA analysis indicated a between group significance at 3 hours post infusion in absolute neutrophils between NAD+ IV and NR IV (4724±2159 and 2883±1184 respectively; p=0.0164), this also shows a clinical significance with the changes in NAD+ IV likely due to inflammation. Baseline absolute neutrophil levels were statistically different in the NR IV group compared to the saline group (2183±858.5; p=0.0203). Absolute eosinophils were significantly different in the NR IV group at all three time points compared to saline (baseline: 112.2±82.69; p=0.0413, 3 hours post infusion: 86.64±60.50; p=0.0448, 24 hours post infusion: 102.5±48.33; p=0.0350). The mean corpuscular volume was significantly different at all three time points for NR IV compared to the saline group (baseline: 91.55±2.306 and 90.85±4.826 respectively; p<0.0001, 3 hours post infusion: 90.54±3.205 and 89.92±4.596 respectively; p<0.0001, 24 hours post infusion: 90.85±2.872 and 90.82±5.055 respectively; p<0.0001). MCV was also significantly different between NAD+ IV and NR IV at all three time points (baseline: 88.43±3.772 and 91.55±2.306 respectively; p<0.0001, 3 hours post infusion: 87.38±3.991 and 90.54±3.205 respectively; p<0.0001, 24 hours post infusion: 87.34±3.035 and 90.85±2.872 respectively; p<0.0001). White blood cell count showed statistically significant differences in the NR IV group compared to saline at baseline (4.236±1.174 and 6.783±2.506 respectively; p=0.0161) and 3 hours post infusion (4.909±1.454 and 7.233±1.908 respectively; p=0.0336). Between group differences were observed at 3 hours post infusion between NAD+ IV and NR IV (6.990±2.386 and 4.909±1.454 respectively; p=0.0249) though these were not deemed clinically significant.

Adverse Events

Participants were monitored for adverse events and for the development of any exclusion criteria during the intervention. One participant in the NR IV group stumbled on a low corner of a bookshelf while engaging in physical activity in the waiting area. This resulted in a small cut, which was treated with a Band-Aid. This AE was classified as mild and was determined to be not related to the intervention. No other AEs were identified during the intervention period or the follow-up period.

NAD+ Analysis

Figure 3:
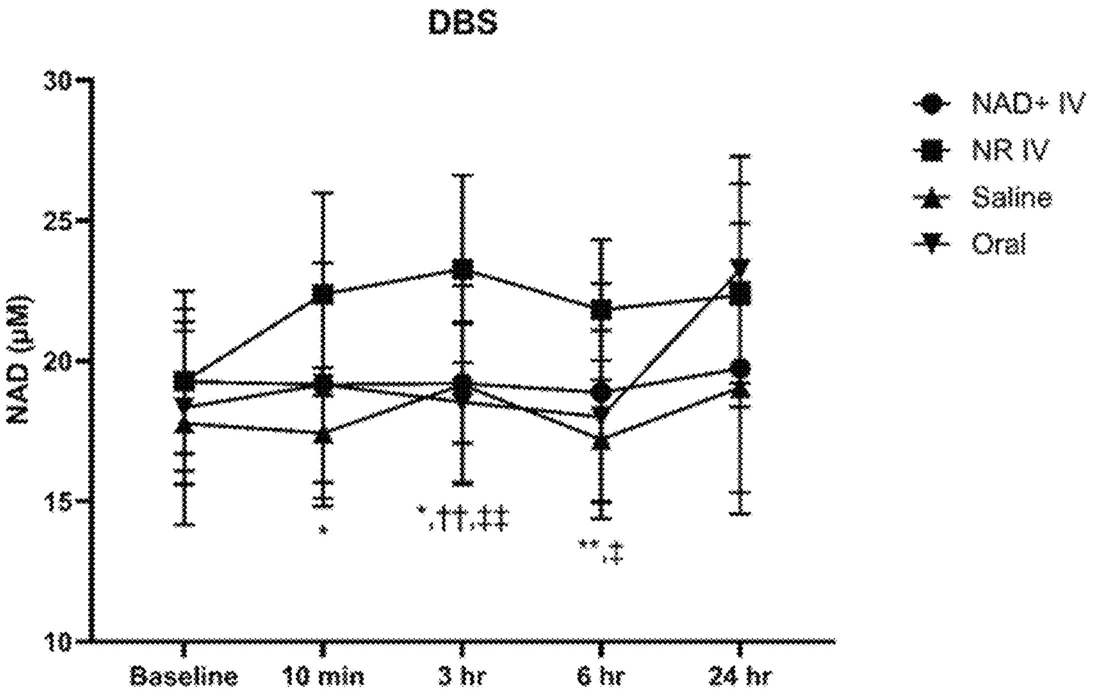
FIG. 3 depicts NAD measurements over time as assessed by dried blood spots (DBS). Dried blood spots were collected at various time points to observe the kinetics of NAD+ changes following interventions with $NAD^+$ IV, NR IV, saline, or oral NR. NAD levels are reported as means with standard deviation. Analysis by ANOVA; *, **=NR IV vs Saline (*p<0.05, **p<0.01); †, ††=NAD+IV vs NR IV (†p<0.05, ††p<0.01); ‡, ‡‡=NR IV vs Oral (‡p<0.05, ‡‡p<0.01).
Figure 4:
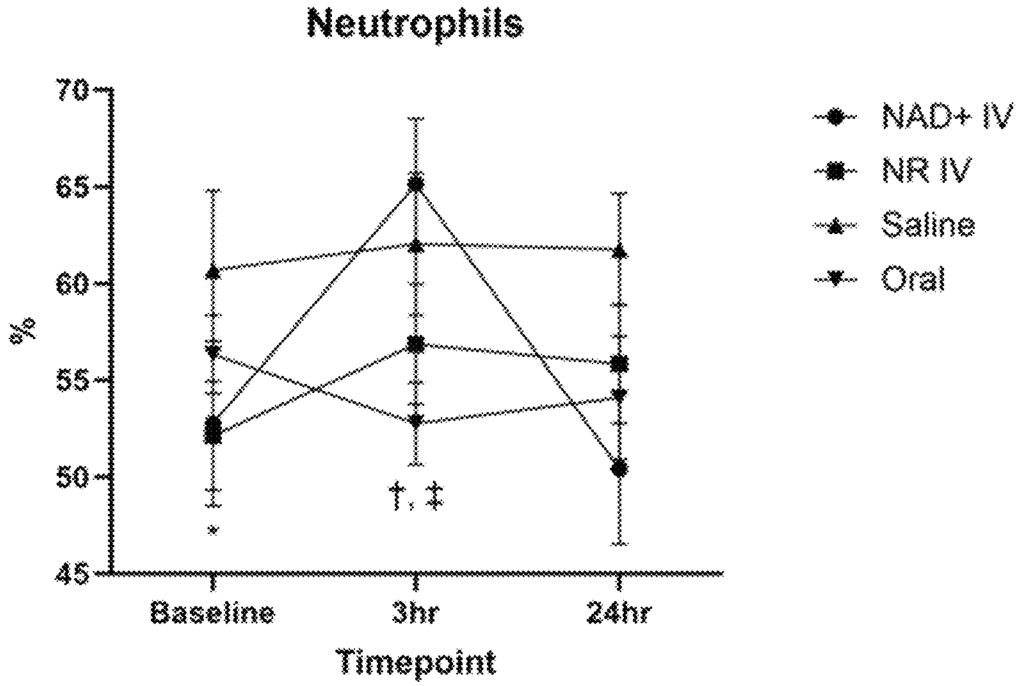
FIG. 4 depicts Hematology measurements of Neutrophils (%) over time in the test groups. Analysis by ANOVA; *=NR IV vs Saline (*p<0.05); †=NAD+IV vs NR IV (†p<0.05); ‡=NR IV vs Oral (‡p<0.05).
Figure 5:
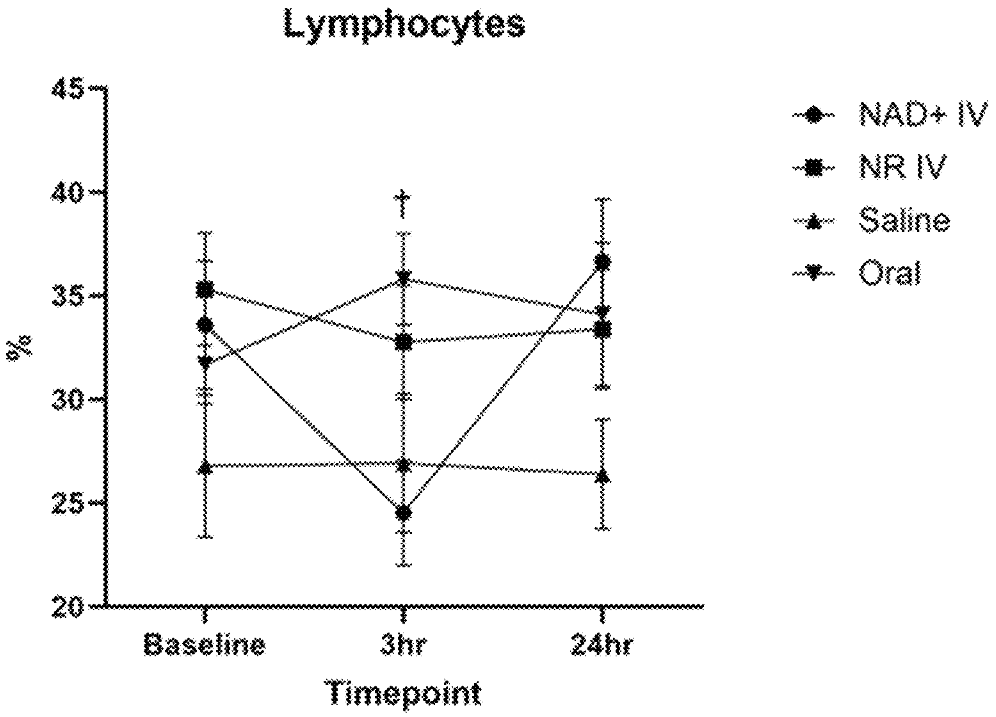
FIG. 5 depicts Hematology measurements of Lymphocytes (%) over time in the test groups. Analysis by ANOVA; ∛=NAD+IV vs NR IV (†p<0.05).
Figure 6:
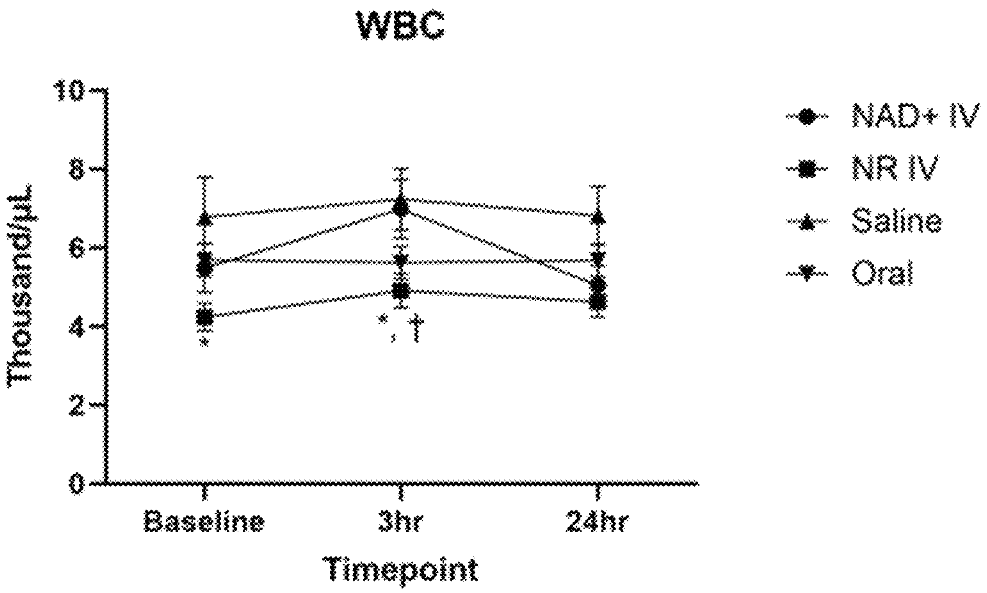
FIG. 6 depicts Hematology measurements of White Blood Cell count (Thousand/microliter) over time in the test groups. Analysis by ANOVA; *=NR IV vs Saline (*$p<0.05$); †=NAD+IV vs NR IV (‡$p<0.05$).
Figure 7:
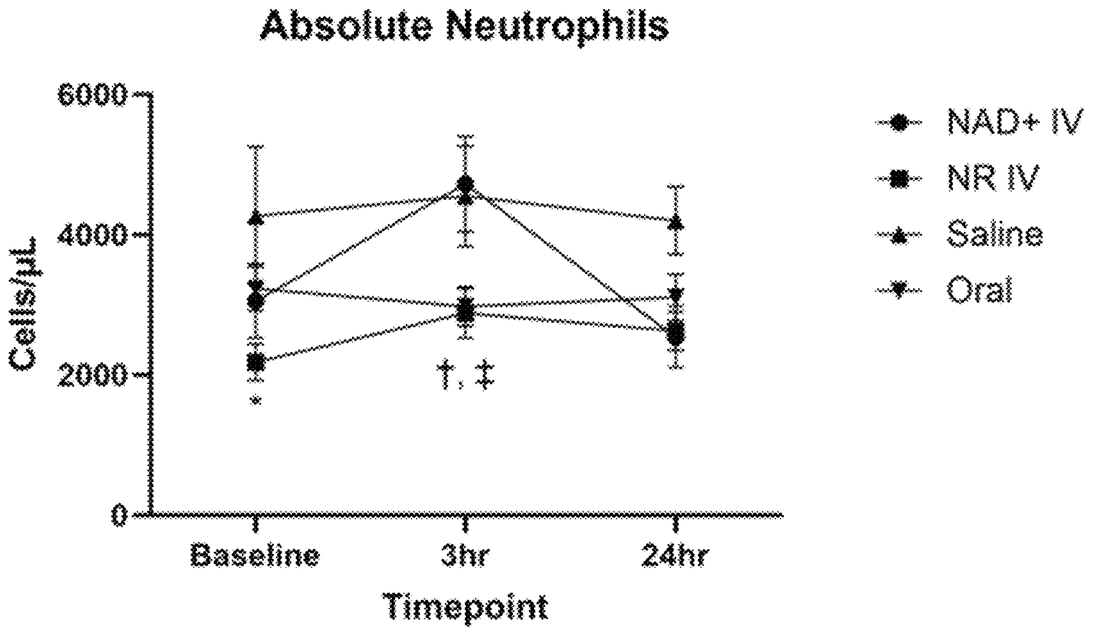
FIG. 7 depicts Hematology measurements of Absolute Neutrophils (Cells/microliter) over time in the test groups. Analysis by ANOVA; *=NR IV vs Saline (*$p<0.05$); †=$NAD^+$ IV vs NR IV (†$p<0.05$); ‡=NR IV vs Oral (‡$p<0.05$).
Figure 8:
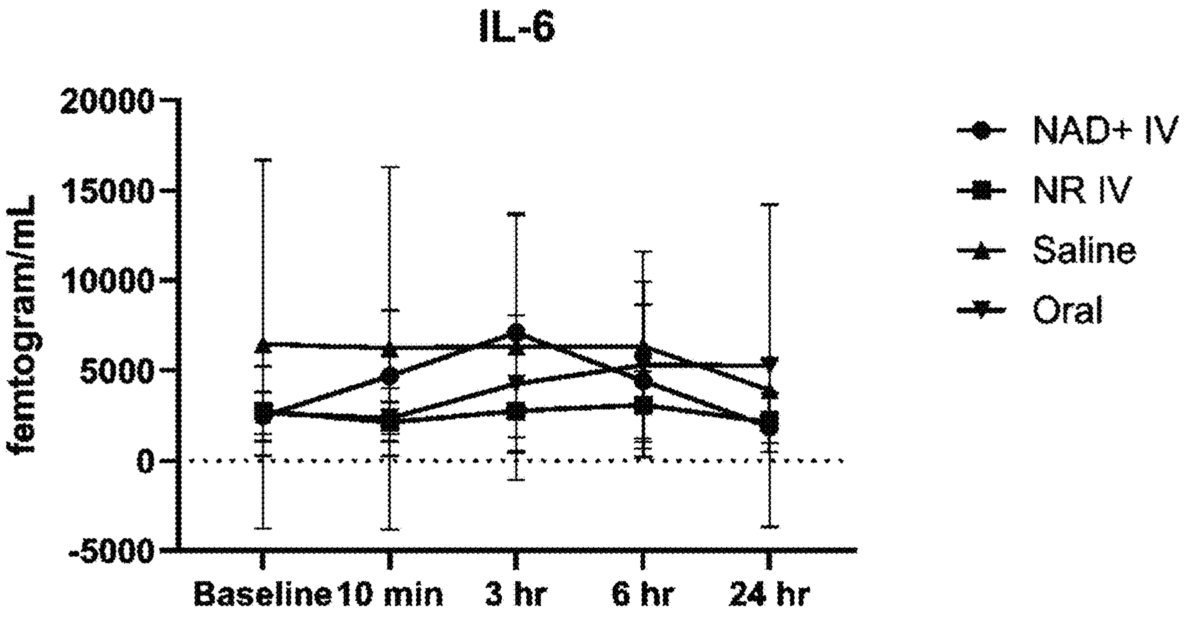
FIG. 8 depicts the measurements of IL-6 inflammatory marker (femtogram/mL) over time in the test groups. The levels were measured using a custom Mesoscale discovery S-PLEX Proinflammatory kit.
Figure 9:
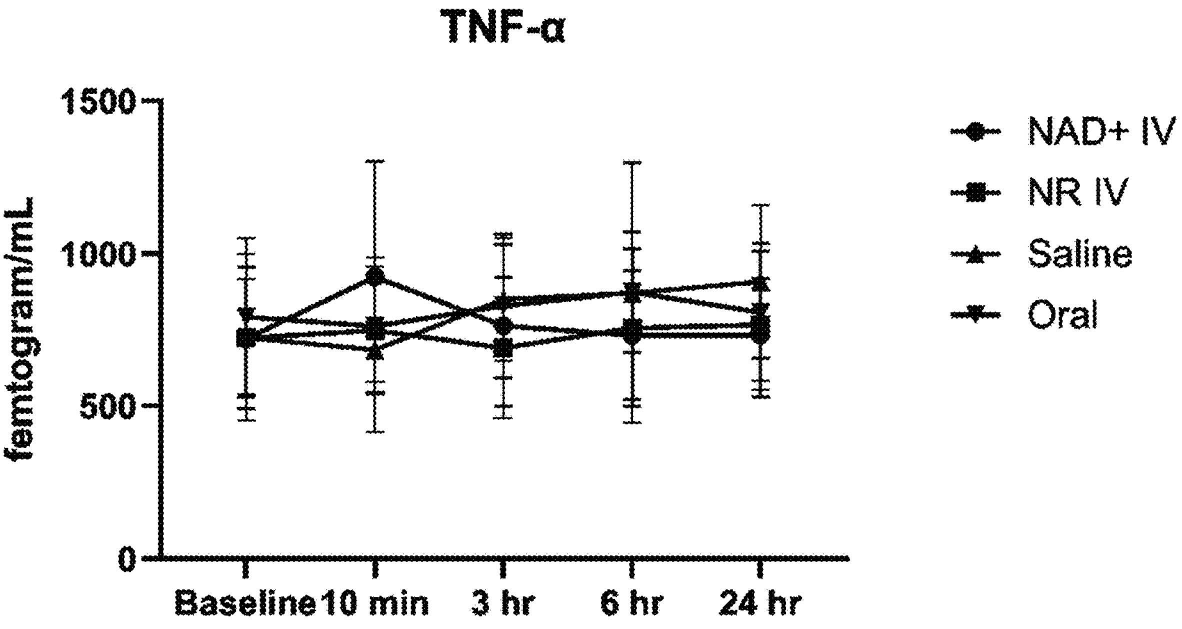
FIG. 9 depicts the measurements of TNF-alpha inflammatory marker (femtogram/mL) over time in the test groups. The levels were measured using a custom Mesoscale discovery S-PLEX Proinflammatory kit.

The use of dried blood spots (DBS) allowed for the analysis of NAD+ levels based upon samples that could be prepared at the clinic or by the study participants from home. While 36 of 37 participants in study 1 utilized the DBS at all time points, not all samples were analyzable. For the baseline DBS collected for NAD+ IV, NR IV, saline, and oral NR, the usable samples were (n=6,6,4,8), at t=10 minutes after the completion of the infusion (n=9,7,6,7), at t=3 hours (n=8,9,6,8), at t=6 hours (n=9,9,6,10); at t=24 hours (n=8, 8,5,8), respectively (FIG. 3). NAD+ IV does not appear to increase whole blood NAD+ until 24 hours, with a 2%, average increase, relative to baseline. For NR IV, NAD+ levels appeared to peak at 3 hours with a 20.7% increase compared to baseline, which was decreased to 16% at 24 hours. When comparing the between-group analyses, there were not statistically significant differences (ANOVA) at baseline, 24-hours ($p=0.242$; $R_2=0.151$). However, the model was significant for the 3-hour timepoint ($p=0.010$; $R_2=0.337$), as significant differences were observed between the NAD+ and NR IV group ($t=2.81$, $p=0.009$), between the NR-IV and saline groups ($t=-2.63$, $p=0.014$), and between the NR IV and oral NR groups ($t=-3.27$, $p=0.003$) and at 6-hours ($p=0.032$; $R_2=0.251$). Thus, NR IV resulted in a statistically significant increase in whole blood NAD+ at 3 hours, relative to the placebo and NAD+ IV groups. At 6 hours, near-significant differences were observed between the NAD+ and NR IV group ($t=1.99$, $p=0.055$), and significant differences were observed between the NR IV and saline groups ($t=-2.80$, $p=0.009$), and between the NR IV and oral NR groups ($t=-2.59$, $p=0.015$). See, Tables 3-9 below.

Dried Blood Spot Results

Tables 3-9 below reflect mean/SD for each group at each of the 7 timepoints. A basic ANOVA was conducted to investigate the data.

TABLE 3

Baseline Scores

| Test group | Mean NAD | SD | Frequency |
|---|---|---|---|
| NAD+ | 19.27 | 2.58 | 6 |
| NR - IV | 19.28 | 3.20 | 6 |
| Saline | 17.78 | 3.62 | 4 |
| NR - Oral | 18.34 | 2.73 | 8 |

* (n = 24). There was no significant difference between any of the groups at baseline.

TABLE 4

Immediately Post-Intervention Scores

| Test group | Mean NAD | SD | Frequency |
|---|---|---|---|
| NAD+ | 19.16 | 4.33 | 9 |
| NR - IV | 22.38 | 3.60 | 7 |
| Saline | 17.43 | 2.32 | 6 |
| NR - Oral | 19.16 | 3.49 | 8 |

* (n = 30). The model was not significant for the immediate timepoint (p = .115; R2 = .201). However, significant differences were observed between the NR-IV and saline groups (t = - 2.46, p = .021). Scores between the NAD+ and NR-IV groups were approaching significance (t = 1.76, p = .089) and between the oral NR and NR-IV group (t= −1.72; p = .098).

TABLE 5

3 Hours Post-Intervention Scores

| Test group | Mean NAD | SD | Frequency |
|---|---|---|---|
| NAD+ | 19.20 | 2.13 | 8 |
| NR - IV | 23.28 | 3.34 | 9 |
| Saline | 19.15 | 3.54 | 6 |
| NR - Oral | 18.54 | 2.87 | 8 |

* (n = 31).

* The model was significant for the 3 hour timepoint (p = .010; R2 = .337). Significant differences were observed between the NAD+ and NR-IV group (t = 2.81, p = .009), between the NR-IV and saline groups (t = −2.63, p = .014), and between the NR-IV and oral NR groups (t = −3.27, p = .003).

TABLE 6

6 Hours Post-Intervention Scores

| Test group | Mean NAD | SD | Frequency |
|---|---|---|---|
| NAD+ | 18.88 | 3.89 | 9 |
| NR - IV | 21.83 | 2.50 | 9 |
| Saline | 17.20 | 2.82 | 6 |
| NR - Oral | 18.01 | 3.07 | 10 |

* (n = 34).

* The model was significant for the 6 hour timepoint (p = .032; R2 = .251). Near-significant differences were observed between the NAD+ and NR-IV group (t = 1.99, p = .055), and significant differences were observed between the NR-IV and saline groups (t = −2.80, p = .009), and between the NR-IV and oral NR groups (t = −2.59, p = .015).

TABLE 7

24 Hours Post-Intervention Scores

| Test group | Mean NAD | SD | Frequency |
|---|---|---|---|
| NAD+ | 19.73 | 5.18 | 8 |
| NR - IV | 22.34 | 3.98 | 8 |
| Saline | 19.06 | 3.74 | 5 |
| NR - Oral | 23.25 | 4.04 | 8 |

* (n = 29).

* The model as a whole was not significant for the 24-hour timepoint (p = .242; R2 = .151).

Discussion

NAD+ is an essential coenzyme required for cellular functions and health maintenance. During aging, the accumulation of metabolic stressors that activate NAD+ consuming enzymes, including CD38 and poly (ADP-ribose) polymerases (PARPs) likely result in or contribute to the decline in NAD+ availability (McReynolds et al., Age-related NAD+ decline. *Exp Gerontol* (2020) 134:110888). While the definition of 'normal' NAD+ levels in blood and tissue has yet to be determined scientifically, it is broadly recognized that the maintenance of sufficient intracellular NAD+ pools is required for optimal health.

The clinical use of intravenous NAD+ in the United States was popularized by Paula Norris Mestayer and Dr. Richard Mestayer of the Springfield Wellness Center in the early 2000s and is now offered at clinics throughout the world to treat specific addictions and neurological conditions, as well as general wellness support. Despite its popularity, the science behind the safety and efficacy of NAD+ IV is minimal. Moreover, on a mechanistic basis, there is concern that the presence of increased eNAD+ following NAD+ IV administration may be recognized as a pathophysiological signal by the immune system, resulting in an inflammatory response (Adriouch et al., 2012; Audrito et al., The Extracellular NADome Modulates Immune Responses. *Front*

*Immunol* (2021) 12:704779). Anecdotally, the infusions have been described as painful or uncomfortable, causing gastrointestinal disturbances, thereby necessitating an extremely slow rate of administration. Consistent with these reports, Grant et al., A Pilot Study Investigating Changes in the Human Plasma and Urine NAD+ Metabolome During a 6 Hour Intravenous Infusion of NAD+. *Front Aging Neurosci* (2019) 11:257, required an intravenous infusion rate of 2 mg/min over six hours to administer 750 mg of NAD+ to participants without adverse events. The requirement of a six-hour infusion time underscores the time inefficiency of such a method (Grant et al., 2019). In the present study, the tolerance to intravenous NAD+ and NR was variable and individual. The majority of participants reported adverse experiences during the NAD+ IV infusion, e.g., nausea, headache, diarrhea, and muscle tightness, in contrast to reports of tingling and slight nausea and coldness in the NR IV group. In both groups, symptoms were resolved once the infusion was completed. In study 1, the infusion rates were normalized for all participants at the beginning of the infusion to ensure safety, as infusion rates and related side effects have not previously been documented in the literature. Due to the nature of the infusion administration in study 1, study 2 was employed to create a true head-to-head comparison of the infusion tolerance and rate between NAD+ IV and NR IV, as general safety was demonstrated in study 1. As such, it was determined that the average infusion time for NR IV was ¼ of the time for NAD+ IV.

To evaluate the clinical safety of the infusions, the first study examined changes in laboratory metrics relative to the saline control group, 500 mg of NR in the test group, 500 mg of NAD+ as an active comparator, and 500 mg of oral Niagen for bridging the effects of oral and IV administration of NR. The NR IV, saline, and oral group participants did not display any clinically relevant changes in the comprehensive metabolic panel, which included BUN, creatinine, sodium, potassium, calcium, $CO_2$, AST, ALT, Alk Phos, protein, and albumin, or in the CBC with differential. These results are generally consistent with the observations made by Grant et al. in a study investigating the effects of a 6-hour NAD+ IV infusion (Grant et al., 2019). Similarly, intravenous administration of NR was also well-tolerated with no clinically relevant changes in laboratory markers. Unlike Grant et al., 2019, however, who reported statistically significant (though not clinically relevant) changes in circulating bilirubin and AST levels 8 hours after NAD+ IV initiation, significant differences in either indicator of liver function were not detected at the 3- and 24-hour timepoints in the NAD+ IV group. These apparent discordances may potentially be explained by the fact that the blood samples for clinical chemistry measurements were collected at different timepoints, as well as differences in dose utilized between the two studies. Likewise, consistent with findings from previously published clinical studies, oral Niagen ingestion was safe and well tolerated.

Noteworthy were shifts in the upward trends for both glucose and insulin concentrations in all four participant groups, including the controls. These parameters were likely influenced by the consumption of food before the 3-hour assessment, which represented a deviation from the original protocol. Thus, this precludes us from ascertaining the actual effects of the interventions on these blood parameters.

Concerning changes in hematological parameters, the NAD+ IV group notably presented with clinically significant elevations in white blood cells and increases in absolute and percentage neutrophils. The increase in neutrophils from baseline to three-hours post-infusion are commonly attributed to inflammatory responses, physiological or psychological stressors, including immunological responses (Tahir and Zahra, Neutrophilia. Study Guide from StatPearls Publishing, Treasure Island, FL, 26 May 2021). Therefore, these observations are consistent with the notion that NAD+ IV elevates eNAD+ such that it is interpreted by the immune system as a pathological event (Audrito et al., 2021). These changes were not observed in the saline, NR IV group, nor in the oral group.

While hematology and clinical chemistry assessments were not incorporated as part of the inclusion criteria, it is worth noting that the mean $CO_2$ levels were lower than typically seen in clinical practice across all groups; two participants had elevated AST/ALT at baseline and two participants were borderline anemic. Additionally, one participant's glucose and insulin levels at baseline and 24 hours suggest that the fasting protocol was not adhered to, and it is likely that a carbohydrate-rich meal was consumed prior to the test. Additionally, the neutrophil responses for this individual at the three-hour mark suggest that the participant may have been either immunologically dealing with an infection, stress response or other inflammatory response.

The results of the present study are broadly in line with the work of Kimura and colleagues, who, in a single-arm open-label study reported that the intravenous administration of another NAD+ precursor, nicotinamide mononucleotide (NMN, 300 mg dissolved in 100 mL saline, infused at a rate of 5 mL/min) was safe and well-tolerated in 10 healthy Japanese adults without evidence of untoward effects on organ function (Kimura et al., Nicotinamide Mononucleotide Is Safely Metabolized and Significantly Reduces Blood Triglyceride Levels in Healthy Individuals. *Cureus* (2022) 14: c28812). Further, the investigators found that intravenous NMN elevated blood NAD+ levels at multiple timepoints relative to baseline. Similar to NAD+, NMN is a phosphorylated compound that requires extracellular dephosphorylation to form NR or nicotinamide, which are readily taken up by the cell to generate NAD+ (Ratajczak et al., 2016; Anthony A Sauve et al., 2023). Therefore, NR is proposed to represent the more efficient means of boosting the intracellular NAD+ pool, and the health benefits of NMN administration are likely mediated through its requisite extracellular dephosphorylation to NR.

Oral supplementation with NAD+ precursors has increased in popularity over the past decade, as a strategy to support healthy aging. NAD+ is directly or indirectly involved with each of the molecular hallmarks of aging, which describe the cellular mechanisms of the aging processes (López-Otín et al., Hallmarks of aging: An expanding universe. *Cell* (2023) 186:243-278). The use of oral supplementation with NR has become a strategy for elevating NAD+ to support healthy aging. Similarly, the use of intravenous methods to boost NAD+ is increasing in popularity, though the evidence of safety and effectiveness of NAD+ IV has been minimal in the peer-reviewed literature. To date, Ross et al., A pilot study investigating changes in the human plasma and urine NAD+ metabolome during a 6 hour intravenous infusion of NAD+. *Front. Aging Neurosci.* (2019) 11:1-10, has shown an increase in NAD+ in the plasma after NAD+ IV infusion, but prior to this article, such information pertaining to the changes in whole blood have not been described. In this study, NAD+ IV did not significantly elevate whole blood NAD+ within 24 hours. It is hypothesized that the infusion of NAD+ results in a rise in extracellular NAD+, triggering an immune response that results in the adverse physical experiences (Adriouch et al., 2001; Liu et al., 2001). For all groups, there was a mean whole blood NAD+ increase, which could be explained by an increase in hydration from the saline, for all but the oral group. The mechanisms resulting in the mild tingling experienced by the NR IV participants are not yet known, though the level of tingling appeared to be greater when the infusion rates were faster. NRIV resulted in a statistically significant increase in whole blood NAD+ compared to NAD+IV and the saline control at 3 hours, and a statistically significant increase at 6 hours compared to saline, which was near significant (p=0.055) when comparing to NAD+ IV. The pharmacokinetics of NR IV and oral NR were different in this study, as IV NAD+ appeared to reach a maximum concentration ($C_{max}$) at 3 hours, whereas oral NR $C_{max}$ was observed at the 24-hour timepoint. This appears different than previous assessments, where a single oral dose of 1000 mg of NR resulted in a $C_{max}$ at 9 hours (n=1) in human peripheral blood mononuclear cells (Trammell et al. 2016a) and at 3 hours on Day 9 of a supplementation study (Airhart et al. 2017). These differences are likely explained by variations in dosing, biofluids sampled, and in the later study, protocol differences, as whole blood NAD was not measured on Day 1 in the naïve participants. Future clinical research will benefit from more study participants to improve the statistical power for these analyses.

Limitations

An a priori statistical power analysis was not conducted for the current study, as this was a phase 0/1 assessment, and such head-to-head comparisons were not available in the literature in clinical or preclinical models. Though the population selected was determined to be healthy, a couple of participants were anemic/borderline anemic, and a couple had baseline elevated liver enzymes. In clinical trials, controlling for hydration status when collecting serum samples is important, as most tests are a unit of measure, often weight or number per dilution status. (e.g., ng/dl or a number of cells per microliter). This control ensures the accuracy and reliability of the results. Additionally, the allowance of the consumption of food and beverages, while controlled, before the three-hour assessments confounded the results for glucose and insulin. The study results suggest that the NAD+ infusion may have resulted in an inflammatory response due to the increase in neutrophils 3 hours after the infusion in these participants. To validate these results, it is suggested that future studies incorporate additional clinical parameters of inflammation, including c-reactive protein, erythrocyte sedimentation rate, procalcitonin, calprotectin, and plasma viscosity, or the assessment inflammatory cytokines in plasma or serum.

Concerning the treatment dose, this study only compared a single infusion of each of the interventions, though in clinics, NAD+ may be offered at various doses from 250-1250 mg/day, as well as infused or injected over multiple days. To improve ecological validity, future studies would benefit from assessing multiple infusions as well as varying doses. In this study, mass equivalents of NR and NAD+ were utilized. The scientific community has not validated the presence of a cellular NAD+ transporter, thus NAD+ requires the release of its two phosphate groups, ultimately entering the cell as nicotinamide or nicotinamide riboside (Nikiforov et al., 2011). Direct comparison of molecular equivalents of NR and NAD+ is needed, as well as analyses of NAD+ from muscle and skin biopsies and other biofluids to determine why NAD+ IV failed to alter whole blood NAD+. It may also be beneficial to evaluate infusions followed by oral administration of NR to determine if oral supplementation is able to sustain elevations in NAD+ between infusion.

The NAD+ dried blood spots, while convenient for at home sampling, did not result in 100% usable samples. There were some initial challenges in understanding the instructions and ensuring that multiple blood drops did not touch in the designated locations on the cards. When blood samples overlapped or there were other deficits in the sample collection, these samples were unusable, and thus were excluded from the analysis.

Conclusions

This is the first study to clinically evaluate nicotinamide riboside (NR) administered through an intravenous infusion. The acute intravenous infusions of 500 mg of pharmaceutically prepared NR IV were safe in the study participants, with minor infusion-related temporary experiences and no attributable adverse events for up to 14 days post-infusion. In comparison to NAD+ IV, NR IV was infused faster, and the infusion experience was more tolerable. NR IV increased NAD+ levels within 24 hours, which was surprisingly not observed with NAD+ IV. For future studies, is it recommended that protocols that provide multiple infusions of NAD+ are substituted with NR IV to determine if nicotinamide riboside can provide the same or greater benefits as NAD+ IV, but with fewer side effects and faster infusion rates.

In other embodiments, it is expected that other NAD+ precursors such as, for example, nicotinyl riboside compounds selected from nicotinic acid riboside (NAR, II), nicotinamide mononucleotide (NMN, III), Reduced nicotinamide mononucleotide (NMNH), nicotinic acid mononucleotide (NaMN, IV), Reduced nicotinic acid mononucleotide (NaMNH), reduced nicotinamide riboside (NRH, V), reduced nicotinic acid riboside (NARH, VI), NR triacetate (NRTA, VII which is a species of Ia), NAR triacetate (NARTA, VIII), NRH triacetate (NRH-TA, IX), or NARH triacetate (NARH-TA, X), and salts, solvates, or mixtures thereof, or derivatives thereof, would have similar or better benefits as was observed for NR-IV compared to NAD-IV.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments the values may range in value either above or below the stated value in a range of approximately ±5%; in other embodiments the values may range in value either above or below the stated value in a range of approximately ±2%; in other embodiments the values may range in value either above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

We claim:

1. A method for administration of nicotinamide riboside, a salt thereof, or a solvate thereof to a human subject, comprising the steps of: (a) providing a sterile aqueous-based I.V. or injectable formulation containing NR, a salt thereof, or a solvate thereof; and (b) intravenously, subcutaneously, parenterally, or intramuscularly administering the formulation to the human subject by injection or infusion in an amount effective to reduce one or more side effects causing discomfort and/or maintain a comfort level in the human subject, wherein the sterile aqueous I.V. or injectable formulation is administered over about 0.5 hours to about 3 hours.

2. The method of claim 1, further comprising step (c):

(c) continuously measuring and monitoring the side effects and/or comfort level of the human subject during the administration of the formulation to ensure that the side effects are reduced.

3. The method of claim 1, wherein the one or more side effects causing discomfort are selected from the group consisting of a pain response, burning sensation, generalized discomfort, headache, nausea, gastrointestinal discomfort, gastrointestinal upset, cramps, nerve tingling, chest discomfort, labored breathing, and muscle weakness.

4. The method of claim 2, wherein the side effect of steps (b) and (c) is a pain response which is minimized during and after administration of the sterile aqueous formulation.

5. The method of claim 1, wherein the side effect is a generalized discomfort which is minimized during and after administration of the sterile aqueous formulation.

6. The method of claim 1, wherein the nicotinamide riboside salt is a chloride salt (NR-Cl).

7. The method of claim 1, wherein the nicotinamide riboside salt is selected from the group consisting of bromide, iodide, fluoride, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfate, tartrate, hydrogen tartrate, malate, hydrogen malate, maleate, fumarate, citrate, stearate, palmitate, myristate, laurate, caprate, caprylate, caproate, oleate, linoleate, sulfonate, trifluoromethanesulfonate, trichloromethanesulfonate, tribromomethanesulfonate, trichloroacetate, tribromoacetate, and trifluoroacetate.

8. The method of claim 6, wherein the nicotinamide riboside chloride salt is crystalline Form I, Form II, or a combination thereof, or a lyophilized or freeze-dried powder thereof.

9. A method for administration of nicotinamide riboside, a salt thereof, or a solvate thereof to a human subject, comprising the steps of: (a) providing a sterile aqueous-based I.V. or injectable formulation containing NR, a salt thereof, or a solvate thereof; and (b) intravenously, subcutaneously, parenterally, or intramuscularly administering the formulation to the human subject by injection or infusion in an amount effective to reduce one or more side effects causing discomfort and/or maintain a comfort level in the human subject, wherein the sterile aqueous I.V. or injectable formulation is administered over less than about 0.5 hour.

10. The method of claim 6, wherein the NR-Cl is administered in a daily dose of from about 25 mg to about 3000 mg.

11. The method of claim 6, wherein the NR-Cl is administered in a daily dose of from about 500 mg to about 1000 mg for intravenous administration.

12. The method of claim 1, wherein the aqueous-based I.V. or injectable formulation further contains a compound selected from the group consisting of nicotinamide adenine dinucleotide (NAD+),-(2',3',5'-triacetyl-beta-D-ribofuranosyl)-nicotinamide (NRTA), Nicotinic acid riboside (NAR), Reduced nicotinamide mononucleotide (NMNH), Nicotinamide Mononucleotide (NMN), Nicotinic acid mononucleotide (NaMN), Reduced nicotinic acid mononucleotide (NaMNH), Reduced nicotinamide riboside (NRH), Reduced nicotinic acid riboside (NARH), 1-(2',3',5'-triacetyl-beta-d-ribofuranosyl)-nicotinic acid (NARTA), 1-(2',3',5'-triacetyl-beta-d-ribofuranosyl)-1,4-dihydronicotinamide (NRH-TA), and 1-(2',3',5'-triacetyl-beta-d-ribofuranosyl)-1,4-dihydronicotinic acid (NARH-TA), or salts thereof.

13. The method of claim 12, wherein the one or more side effects measured during step (b) is reduced.

14. The method of claim 9, wherein the nicotinamide riboside salt is a chloride salt (NR-Cl).

* * * * *